(12) United States Patent
Takenaka et al.

(10) Patent No.: US 9,783,518 B2
(45) Date of Patent: Oct. 10, 2017

(54) THERAPEUTIC AGENT AND TREATMENT METHOD FOR AMELIORATING UREMIA

(75) Inventors: Masahiko Takenaka, Fukuyama (JP); Yoshihisa Yamane, Fuchu (JP); Nobutaka Ida, Fujisawa (JP); Hajimu Kurumatani, Fujisawa (JP)

(73) Assignee: Toray Industries, Inc. (JP)

( * ) Notice: Subject to any disclaimer, the term of this patent is extended or adjusted under 35 U.S.C. 154(b) by 573 days.

(21) Appl. No.: 11/988,423

(22) PCT Filed: Jul. 7, 2006

(86) PCT No.: PCT/JP2006/313572
§ 371 (c)(1),
(2), (4) Date: May 5, 2008

(87) PCT Pub. No.: WO2007/007668
PCT Pub. Date: Jan. 18, 2007

(65) Prior Publication Data
US 2009/0143463 A1 Jun. 4, 2009

(30) Foreign Application Priority Data
Jul. 8, 2005 (JP) .................................. 2005-200888

(51) Int. Cl.
| | | |
|---|---|---|
| *A01N 43/00* | (2006.01) |
| *A61K 31/33* | (2006.01) |
| *C07D 307/93* | (2006.01) |
| *A61K 31/5578* | (2006.01) |
| *A61K 31/5585* | (2006.01) |

(52) U.S. Cl.
CPC ........ *C07D 307/93* (2013.01); *A61K 31/5578* (2013.01); *A61K 31/5585* (2013.01)

(58) Field of Classification Search
None
See application file for complete search history.

(56) References Cited

U.S. PATENT DOCUMENTS

| | | | | | |
|---|---|---|---|---|---|
| 4,022,883 | A | * | 5/1977 | Setala ........................ | 424/93.3 |
| 4,474,802 | A | | 10/1984 | Ohno et al. | |
| 4,752,619 | A | * | 6/1988 | Walser et al. ................ | 514/564 |
| 5,182,266 | A | * | 1/1993 | Kleinert ........................ | 514/18 |
| 5,276,031 | A | * | 1/1994 | Kleinert ...................... | 514/237.2 |
| 5,393,742 | A | * | 2/1995 | Ishii et al. ...................... | 514/23 |
| 5,968,966 | A | * | 10/1999 | Bergstrom .................... | 514/400 |
| 6,558,667 | B2 | * | 5/2003 | Nakanishi ...................... | 424/126 |
| 6,653,345 | B2 | | 11/2003 | Kurumatani et al. | |
| 2003/0092760 | A1 | * | 5/2003 | Kurumatani et al. ........... | 514/468 |

FOREIGN PATENT DOCUMENTS

| | | |
|---|---|---|
| EP | 1 016 408 A1 | 7/2000 |
| EP | 1 106 176 A1 | 6/2001 |
| JP | 1-53672 B2 | 11/1989 |
| JP | 3-163023 A | 7/1991 |
| WO | WO 99/13880 A1 | 3/1999 |
| WO | WO 00/67748 A1 | 11/2000 |
| WO | WO 2004/098611 A1 | 11/2004 |

OTHER PUBLICATIONS

Eduardo Villa et al., American Journal of Hypertension, vol. 6, No. 4, Apr. 1993, pp. 253-257.*
T. Inuki et al., Japanese Pharmacology and Therapeutics, 26/11, 1988, pp. S31-S34, abstract.*
Masateru Yamada et al., European Journal of Pharmacology, 449(1-2), Aug. 2, 2002, pp. 167-176, abstract.*
M. Tobimatsu et al., Annals of Surgery, 209/1, 1988, pp. 65-70, abstract.*
Griffiths et al., "Formation of 6-keto prostaglandin E1 in mammalian kidneys," Br. J. Pharmac. (1983), 79, 149-155.*
Lariviére, R. et al., "Thromboxane Blockade Reduces Blood Pressure and Progression of Renal Failure Independent of Endothelin-1 in Uremic Rats," *Prostaglandins, Leukotrienes and Essential Fatty Acids*, 2004, vol. 71, pp. 103-109.
Tomida, T. et al., "Altered Expression of Prostacyelin Synthase in a Subset of the Thick Ascending Limb Cells and Mesangial Cells in 5/6-Nephrectomized Rats," *Hypertens Res.*, 2001, vol. 24, pp. 411-419.
Vanholder, R. et al., "Review on uremic toxins: Classification, concentration, and interindividual variability", *Kidney International*, 2003, vol. 63, pp. 1934-1943.
Grauer, G. F., Part 5, Chapter 44, "Urologic Diseases", *Small Animal Internal Medicine (Japanese version)*, (R. W. Nelson, C. G. Couto eds.), 2001, pp. 621-636, along with a partial English translation.
Asano, Y., "VII Chronic Renal Failure", *Nephrology* (Kiyoshi Kurokawa eds.), 2001, pp. 345-351 & 362-369, along with a partial English translation.
Koide, K., "1: What is Chronic Renal Failure", *Chemotherapies of Chronic Renal Failure* (Keizo Koide and Susumu Takahashi eds.), 2000, pp. 1-5, along with a partial English translation.

(Continued)

*Primary Examiner* — Jared D Barsky
(74) *Attorney, Agent, or Firm* — DLA Piper LLP (US)

(57) ABSTRACT

A therapeutic agent and a treatment method for uremia of human and animals, which therapeutic agent can be easily taken, has lower side effects, and which is not expensive in view of medical economics, are disclosed. The therapeutic agent for uremia in patients suffering from chronic renal failure comprises as an effective ingredient a prostaglandin $I_2$ derivative having a specific structure, such as beraprost sodium. The therapeutic agent for uremia ameliorates the uremia concurred in patients with chronic renal failure without accompanying side effects, and restoration of decreased appetite, improvements in activities, increase in body weight and the like are achieved. The therapeutic effect of uremia is clear alleviation or disappearance of symptoms of uremia grasped as clinical symptoms, observed in the state of renal failure, especially even in spite of the state wherein the decrease in renal function is progressed.

7 Claims, 8 Drawing Sheets

(56) References Cited

OTHER PUBLICATIONS

Utsunomiya, Y. et al., "Attenuation of immune complex nephritis in NZB/W $F_1$ mice by a prostacyclin analogue", *Clin. Exp. Immunol.*, 1995, 99, pp. 454-460.

Kushiro, M. et al., "Therapeutic effects of prostacyclin analog on crescentic glomerulonephritis of rat", *Kidney International*, 1998, vol. 53, pp. 1314-1320.

Stier, C. T. et al., "Beneficial Action of Beraprost Sodium, a Prostacyclin Analog, in Stroke-Prone Rats", *J. Cardiovascular Pharmacology*, 1997, vol. 30, pp. 285-293.

Owada, A. et al., "Effect of Long-Term Administration of Prostaglandin $I_2$ in Incipient Diabetic Nephropathy", *Nephron*, 2002, 92(4), pp. 788-796.

Robles, R. G. et al., "Effect of cicaprost on the progression of diabetic nephropathy in uninephrectomized streptozotocin-induced diabetic rats", *J. Hypertens. Suppl.*, 1993, vol. 11, 5:S208.

Poelstra, K. et al., "Attenuation of Anti-Thy1 Glomerulonephritis in the Rat by Anti-Inflammatory Platelet-Inhibiting Agents", *Am. J. Pathol.*, 1993, vol. 142, pp. 441-450.

Series, C. et al., "Prostacyclin in the treatment of hemolytic-uremic syndrome: apropos of a case", *Rev. Med. Interne.*, 1996, 17, pp. 76-78, abstract only.

Siegler, R. L. et al., "Renal Prostacyclin Biosynthesis in a Baboon Model of Shiga Toxin Mediated Hemolytic Uremic Syndrome", *Nephron*, 2002, 92, pp. 363-368, abstract only.

Mitra, D. et al., "Thrombotic Thrombocytopenic Purpura and Sporadic Hemolytic-Uremic Syndrome Plasmas Induce Apoptosis in Restricted Lineages of Human Microvascular Endothelial Cells", *Blood*, 1997, 89, pp. 1224-1234.

Adler, S. et al,. "Glomerular Endothelial Cell Injury Mediated by Shiga-Like Toxin-1", *Kidney & Blood Pressure Research*, 1998, 21, pp. 13-21, abstract only.

DiBartola, S. P. et al., "Clinicopathologic findings associated with chronic renal disease in cats: 74 cases (1973-1984)", *J. Am. Vet. Med. Assoc.*, 1987, 190, pp. 1196-1202, abstract only.

Lulich, J. P. et al., "Feline Renal Failure: Questions, Answers, Questions", *The Compendium, Continuing Education Article #1*, 1992, vol. 14, No. 2, pp. 127-153.

Inoue, T. et al., "Jinshikkan no Chiryo (3) Mansei Jinfuzen" Iyaku to Yakugaku, 2002, vol. 47, No. 5, pp. 711-718, along with a partial English.

Lariviére, R. et al., "Thromboxane Blackade Reduces Blood Pressure and Progression of Renal Failure Independent of Endothelin-1 in Uremic Rats," *Prostaplandins, Leukotrienes and Essential Fatty Acids*, 2004, vol. 71, pp. 103-109.

Tomida, T. et al., "Altered Expression of Prostacyclin Synthase in a Subset of the Thick Ascending Limb Cells and Mesanglal Cells in 5/6-Nephrectomized Rats," *Hypertens Res.*, 2001, vol. 24, pp. 411-419.

Fujita, T. et al., "$PGI_2$ analogue mitigates the progression rate of renal dysfunction improving renal blood flow without glomerular hyperfiltration in patients with chronic renal insufficiency," *Prostaglandins, Leukotrienes and Essential Fatty Acids* (2001) 65 (4), p. 223-227.

\* cited by examiner

THERAPEUTIC AGENT AND TREATMENT METHOD FOR AMELIORATING UREMIA

TECHNICAL FIELD

The present invention relates to a therapeutic agent and a treatment method for ameliorating symptoms of uremia in a patient suffering from chronic renal failure.

BACKGROUND OF THE INVENTION

Uremia is a syndrome showing various clinical symptoms stemmed from dysfunctions of various organs and tissues, caused by the toxic components in the urine accumulated in the blood. Uremia occurs when urine cannot be excreted from the body due to failure of renal function irrespective of the primary disease. Uremia has a wide variety of clinical symptoms including gastrointestinal abnormalities such as anorexia, nausea, vomiting, stomatitis and enteritis; nervous system abnormalities such as apathy, unconcern, deterioration of memory, depressed state and coma; circulatory abnormalities such as anemia, erythropoietic disorders, hypertension, ischemic heart diseases, pericarditis and myocarditis; pigmentation; itching; skin abnormalities such as subcutaneous hemorrhage and so on. Uremia is caused by uremic substances accumulated in the blood. It is thought that there are several tens or more uremic substances at present, including, for example, methylguanidine, indole compounds, malondialdehyde, creatinine, β-aminoisobutyric acid, transketolase inhibitors, polyamines, lipolytic inhibitors, urea, and phenols (see, for example, Non-patent Literature 1).

However, it has not yet been clarified which substance, among these uremic substances, essentially participates in the onset of uremic symptoms. Further, although it has not been clarified whether uremia is caused by a single substance or by compound effect of a plurality of these substances, it is thought that the probability of the latter is higher. These facts clearly indicate the difficulty in therapy of uremia by drugs. Anyway, unless the uremic substances are excreted from the body or unless the blood levels of the uremic substances are lowered by an appropriate means, the patient with uremia will die. The therapeutic methods said to be effective for the treatment of uremia are kidney transplantation, dialysis and active carbon preparation treatment. The advantage of the therapeutic methods common to the latter two methods is that a plurality of uremic substances including unknown substances can be removed or diluted nonspecifically by a physical means. However, the methods have drawbacks described below.

Active carbon preparation is orally administered. The mechanism of action of the active carbon preparation is based on the adsorption of various uremic substances generated in digestive organs and excretion thereof from the body. Thus, although the active carbon preparation is called an oral drug, the therapy may be considered as a physical therapeutic method similar to the dialysis treatment described below. Since the active carbon preparation has drawbacks in that taking is not easy, it has a strong tendency to induce constipation, and so on, in addition to the limited therapeutic effect, the therapeutic method is not satisfactory at all.

Dialysis is said to be the most effective therapeutic method for uremia. In fact, by excreting uremic substances by dialysis treatment, the death of the patient due to the uremic substances can be avoided even if the kidney function has been abolished. However, complications by dialysis treatment have been recognized as new problems. For example, complications of long-term dialysis include anemia, renal osteodystrophy, stomach cancer, pericarditis, aluminum osteodystrophy, amyloidosis, crystal arthritis, multiple polycystic kidney and so on. There are also problems of poor QOL of the patients in social life due to the necessity to frequently go to dialysis facilities, and high cost which is a problem in medical economics.

A method called "internal dialysis" has been reported, in which nonprotein nitrogen is medicinally transferred to intestinal tract without a physical means (Patent Literature 1). This is a phenomenon that upon administration of a 15-keto-16-halogen-prostaglandin $E_2$, serum creatinine (Cre) and blood urea nitrogen (BUN) in the blood are transferred to the intestinal tract together with water by enteropooling action (an action to accumulate water in the intestinal tract). However, since enteropooling is an action to accumulate water in the intestinal tract, it necessarily accompanies diarrhea, and the reporter also refers to this point. No matter how much the serum Cre value and BUN value in the blood are decreased, to perform this therapy which accompanies the physical exhaustion and the risk of dehydration due to diarrhea imposes a very heavy burden on the patients with chronic renal failure, so that it is not acceptable at all.

Accordingly, creation of a therapeutic method and therapeutic agent for uremia, free from the above-described problems is demanded.

Although uremia occurs with the progress of renal failure, both of these are syndromes which are separately defined as described below. Non-patent Literature 2 states "a wide variety of, and sometimes confused, terms are used for expressing the renal function and its deterioration", and defines related terms to clearly distinguish the both. More particularly, it calls attention on the difference between the both stating "Renal failure is the state in which the renal function is decreased and the abnormalities (azotemia and decrease in the ability to concentrate urine) are maintained, and means the function level of the organ rather than a specific disease", and "Uremia indicates the fact that urine exists in the blood" (see Non-patent Literature 2). Other technical books of nephrology also define and describe uremia and renal failure as different "syndromes" and not "names of diseases" (Non-patent Literature 3).

Renal failure is classified into two different syndromes, acute renal failure and chronic renal failure. Acute renal failure suddenly occurs, but in most cases, its renal function impairment is reversible. In fact, effective drugs and therapeutic methods have already existed, and, in many cases, the renal function of the patients may be restored to the normal state by merely removing the cause. On the other hand, as for chronic renal failure, it is difficult to clearly determine the time of onset thereof, and it slowly occurs over several months to several years. Further, the renal damage occurred is irreversible (see, for example, Non-patent Literature 4), and refractory to various drugs and therapeutic methods. Thus, therapy of uremia which occurs with the progress of chronic renal failure is especially important.

As the results of the studies so far using nephritis model animals or renal failure model animals, various prophylactic and therapeutic drugs for chronic renal failure or its primary disease have been found. Various drugs are now clinically used, for example, antiplatelet drugs such as dipyridamole, dilazep hydrochloride, trapidil and aspirin; and anticoagulants such as heparin and warfarin are used for glomerulonephritis; and thiazide diuretics, loop diuretics, angiotensin converting enzyme (ACE) inhibitors, and calcium antagonists such as diltiazem and verapamil are used for cases where the primary disease is essential hypertension. However, any of these is nothing more than a countermeasure which delays the progress of the state of renal failure such as deterioration of renal function and the like, and amelioration or disappearance of uremia by these drugs has not been reported at all.

Among the compounds of General Formula (I) in the present application, beraprost sodium disclosed in Patent Literature 2 has been reported to be effective for primary diseases of chronic renal failure. For example, in a glomerulonephritis model system, Utsunomiya et al. showed that onset of glomerulonephritis can be inhibited by administering beraprost sodium, before onset, to immune complex-induced glomerulonephritis mouse NZB/WF1 which spontaneously develops immune complex-induced glomerulonephritis, using as an index the effect to decrease the urinary excretion of albumin (Non-patent Literature 5). Similarly, Kushiro et al. showed, using rat glomerulonephritis models, that onset of nephritis was prevented by prophylactically administering beraprost sodium to the rats before administering the nephritis-inducing substance, in terms of the effect to decrease the urinary excretion of albumin (Non-patent Literature 6). Stier et al. showed that by administering beraprost sodium together with the supply of saline used as the stimulation inducing hypertension and with feeding of a special diet to the rats which spontaneously develops hypertension, the onset of glomerulonephritis was prevented, based on the urinary protein excretion and an image of the tissue of glomerulus (Non-patent Literature 7). Further, it has been reported that urinary microalbumin in patients with diabetic nephropathy was decreased by the administration of beraprost sodium (Non-patent Literature 8).

Further, there are reports about prostaglandin $I_2$ derivatives (hereinafter also referred to as "$PGI_2$ derivatives" for short) other than the compounds represented by General Formula (I). For example, it is known that cicaprost has an activity to reduce the renal function impairment in streptozotocin-induced diabetic nephropathy rats (Non-patent Literature 9) or the renal function impairment induced by uninephrectomy, high sodium loading and protein loading (Non-patent Literature 10). Similarly, in Thy-1-induced nephritis models, urinary protein is decreased by prophylactically administering iloprost which is a $PGI_2$ derivative before the induction of nephritis (Non-patent Literature 11). Proteinuria is caused by the deterioration of barrier function to macromolecules in the kidney. Therefore, although proteinuria is a good index for examining the glomerulus function which is an aspect of the renal function, proteinuria does not directly determine the severity of uremia. Further, although proteinuria is a good index in early stage of glomerulonephritis, diabetic nephropathy and the like, it is no longer a good index in chronic renal failure because the filtering function to low molecular substances are decreased in chronic renal failure. Further, all of the above-described reports show the prophylactic effects of $PGI_2$ derivatives because the $PGI_2$ derivatives were administered before the onset of nephritis, and do not show the therapeutic effect. Still further, although the reports refer to renal function, they do not refer to or suggest amelioration of uremia at all.

As for the effects of the compounds represented by General Formula (I), there is a report in which rat renal failure models whose primary disease was the nephritis, prepared by administering an antibody to glomerular basement membrane were used (Patent Literature 3). In the report, it was shown that by administering a compound of the General Formula (I) recited in the present application after observing renal failure defined by higher creatinine and BUN, increase in the renal failure markers such as amount of urinary protein excretion, serum Cre value and BUN value was reduced when compared with a control group. Further, it has been reported that clinical administration of beraprost sodium reduced the decrease in renal function in the renal failure in conservative stage, which is indicated by decrease in the creatinine clearance or in the reciprocal of serum creatinine in patients with renal failure (Non-patent Literature 12). However, these reports do not contain any reference or suggestion about uremia or uremic symptoms.

Renal diseases include hemolytic uremic syndrome (HUS) caused by thrombotic microangiopathy. HUS literally shows uremia as its clinical symptom. Series et al. reported that, in one case of HUS, administration of iloprost which is one of the $PGI_2$ derivatives was effective for the improvement of the serum Cre value which is a marker of renal failure (Non-patent Literature 13). However, HUS is a syndrome stemmed from the above-described easily recoverable acute renal failure which is a pathological condition utterly different from uremia in the patients with chronic renal failure whose body homeostasis is drastically impaired, in the resistance to drugs and therapeutic methods. Thus, this report is also totally silent about the applicability to the therapy of uremia in patients with chronic renal failure, which is a severer syndrome.

On the other hand, Siegler et al. reported that $PGI_2$ does not have an activity to inhibit the progress of HUS (Non-patent Literature 14). Even about in vitro studies, there is a report which reports that the ability of vascular endothelial cells to produce $PGI_2$ said to be related to onset of HUS is decreased (Non-patent Literature 15), and a report which reports that no change was observed on the ability to produce $PGI_2$ (Non-patent Literature 16). That is, the pharmacological effect of $PGI_2$ derivatives to HUS is still very unclear, and the above-mentioned Series et al. described that the above-mentioned one case was a very rare case, the relationship between HUS and $PGI_2$ was still contradicting, and frankly concluded that further study was necessary. Anyway, even in HUS which has a better ability to recover the body homeostasis, the involvement of $PGI_2$ is still unclear, and the effectiveness of $PGI_2$ to the uremia of patients with chronic renal failure, whose ability to recover the body homeostasis is much poorer or who have no such an ability, is not expected at all.

As described above, deterioration or amelioration of uremic symptoms in the patients with chronic renal failure by the compounds represented by the General Formula (I), or even by $PGI_2$ derivatives including those other than the compounds represented by the General Formula (I), has not been described at all.

On the other hand, in recent years, increase in the number of patients with chronic renal failure has become a big problem not only in human medicine but also in veterinary medicine. Pet animals such as dogs and cats can now receive highly nutritious diets and high veterinary services. As a result, pet animals came to have a long life similar to humans, and the number of patients suffering from an aging-associated disease or chronic disease which is difficult to cure are now being drastically increased. Chronic renal failure is observed in many kinds of pet animals. Taking cat as an example, comparisons between the chronic renal failure of cats and humans are as follows:

In cats, chronic renal failure occurs at an especially high rate (see, for example, Non-patent Literature 17). In cats of not younger than 15 years old, chronic renal failure amounts to as much as 30% of total diseases, and is a major cause of death of cats (see, for example, Non-patent Literature 18). Further, in very many cases, when a patient cat is carried in an animal hospital, the cat is in considerably progressed state of chronic renal failure, and accompanies uremia.

In general, chronic renal failure of cats is diagnosed by detecting high values of serum creatinine (Cre) and blood urea nitrogen (BUN) value which are clinical markers of renal function, in addition to the past history obtained by hearing and the clinical observations. Abnormal Cre and BUN values are not detected unless 75% of nephron in both kidneys lost its function, and there is a correlation between the magnitude of the abnormal values of the markers of renal function and the ratio of remaining renal function, as in the case of humans.

Uremic symptoms of cats are expressed by nausea, vomiting, diarrhea, anorexia, weight loss, decreased activity, polydipsia and diuresis, intraoral ulcer and so on. Anorexia and shortage of water intake due to the intraoral ulcer also cause dehydration and constipation. After further progress of the diseased state, in addition to anemia, erythropoietic disorders, loss of appetite and depressed state, encephalopathy and neuropathy due to the urine toxin are observed. As described above, the progress of the diseased state of the chronic renal failure and the diversity of the accompanied uremic symptoms are the same as in humans.

Since the cats having progressed uremia tend to develop dehydration, as symptomatic treatments, hydration, and fluid replacement by intravenous or subcutaneous drip infusion for the purpose of dilution of the uremic substances are also performed. For anemia in cats with uremia, erythropoietin having hematopoietic activity is also administered. Since appetite is often reduced also by anemia, an appetite-stimulating treatment is also performed in parallel. For the amelioration of symptoms such as vomiting, diarrhea and stomatitis, symptomatic treatment drugs corresponding to the symptoms are also often used. The individual symptomatic treatments selected for these uremic symptoms are also the same as in the case of human patients with uremia. There is a difference in drug metabolism between cats and humans. For example, acetaminophen which can be safely used in humans induces a serious side effect (acetaminophen poisoning) in cats. In addition to this, a number of antibiotics and anti-inflammatory agents are listed as drugs requiring caution. Further, since the homeostatic functions in the cats showing uremic symptoms are deteriorated, much caution and care are needed for the usage and dosage of the drugs.

Similar to humans, active carbon preparation is used for the therapy of uremia in cats and dogs. The name of the drug for humans is Kremezin and the name of the animal drug is Covalzin. In this therapy, the preparation is orally administered daily, and the substances causing uremia are made to be adsorbed thereto in the digestive tract, and are excreted together with feces. However, similar to humans, taking is not easy and reduction of appetite and constipation are also induced. Further, there is a concern that useful substances may be removed by the nonspecific adsorption of substances.

Similar to humans, dialysis is a very effective therapy of uremia in cats. However, since it is expensive, the therapy has not prevailed to a general therapy. Although kidney transplantation may also be performed in cats as a curative treatment for chronic renal failure and uremia, this has also scarcely spread because it is expensive.

As described above, uremia of animals and humans are similar in various aspects including the state of disease of chronic renal failure, clinical symptoms of accompanying uremia, therapeutic methods, symptomatic treatments and so on. Further, since there are problems in therapeutic methods as in human, creation of an excellent therapeutic method and therapeutic drug for uremia are demanded by the clients (owner) of the patient animals and veterinarians.

Non-patent Literature 1: Vanholder, R. et al., Kidney International, 63, 1934-1943, 2003
Non-patent Literature 2: Grauer, G. F., PART 5, Chapter 44, Urologic Diseases, p 622, In: Small Animal Internal Medicine (Japanese version), R. W. Nelson, C. G. Couto eds., translation supervised by Atsuhiko HASEGAWA and Hajimu TSUJIMOTO, Inter Zoo Tokyo, 2001
Non-patent Literature 3: Yasushi ASANO, VII Chronic Renal Failure, Nephrology (Kiyoshi KUROKAWA eds.), p 345, Nankodo, Tokyo, 2001
Non-patent Literature 4: Keizo KOIDE, 1: What is Chronic Renal Failure, Chemotherapies of Chronic Renal Failure (Keizo KOIDE and Susumu TAKAHASHI eds.), p 1, TOKYOIGAKUSHA, Tokyo, 2000
Non-patent Literature 5: Utsunomiya, Y. et al., Clin. Exp. Immunol., 99, 454-460, 1995
Non-patent Literature 6: Kushiro, M. et al., Kidney International, 53, 1314-1320, 1998
Non-patent Literature 7: Stier, C. T. et al., J. Cardiovascular Pharmacology, 30, 285-293, 1997
Non-patent Literature 8: Owada, A. et al., Nephron, 92(4): 788-796, 2002
Non-patent Literature 9: Robles, R. G. et al., J. Hypertens. Suppl., 11, 5:S208-S209, 1993
Non-patent Literature 10: Villa, E. et al., Am. J. Hypertens., 6, 253-257, 1993
Non-patent Literature 11: Poelstra, K. et al., Am. J. Pathol., 142, 441-450, 1993
Non-patent Literature 12: Fujita, T. et al., Prostaglandins Leukot. Essent. Fatty Acids, October; 65(4):223-227. 2001
Non-patent Literature 13: Series, C. et al., Rev. Med. Interne., 17, 76-78, 1996
Non-patent Literature 14: Siegler, R. L. et al., Nephron, 92, 363-368, 2002
Non-patent Literature 15: Mitra, D. et al., Blood, 89, 1224-1234, 1997
Non-patent Literature 16: Adler, S. and Bollu, R. Kidney & Blood Pressure Research, 21, 13-21, 1998
Non-patent Literature 17: Dibartola, S. P. et al., J. Am. Vet. Med. Assoc., 190, 1196-1202, 1987
Non-patent Literature 18: Lulich, J. et al., The Compendium Continuing Education, 14, 127-152, 1992
Patent Literature 1: JP 3-163023 A
Patent Literature 2: JP 1-053672 B
Patent Literature 3: WO 00/067748

Problems which the Invention Tries to Solve

The problem which the present invention tries to solve is to provide a therapeutic agent and a treatment method for uremia of human and animals, which therapeutic agent can be easily taken, has lower side effects, and which is not expensive in view of medical economics, by which the above-described problems in the prior art are solved, other than physical adsorption of uremic substances and excretion thereof.

Means for Solving the Problems

One of the reasons why the creation of therapeutic agent and therapeutic method of uremia has not achieved in spite of the strong demand is that an appropriate experimental model of uremia has not been established. After a series of investigations and studies, the present inventors focused attention to the fact that patient cats suffering from chronic renal failure accompanying uremia at a high rate come to animal hospitals, and a number of patient cats die because they cannot receive dialysis treatment because of economical or technical reason. In view of this, after intensive studies on patient cats, the present inventors discovered that improvement in renal function is not directly linked to the amelioration of uremia, and the drugs comprising as an effective ingredient a compound represented by the General Formula (I) described below are effective for the therapy of uremia, based on the discovery that uremia may be ameliorated or disappear even under the state that the renal failure markers are continuously increased, thereby completing the present invention.

That is, the present invention provides:

1. A therapeutic agent for uremia in patients suffering from chronic renal failure, the therapeutic agent comprising as an effective ingredient a compound of the General Formula (I):

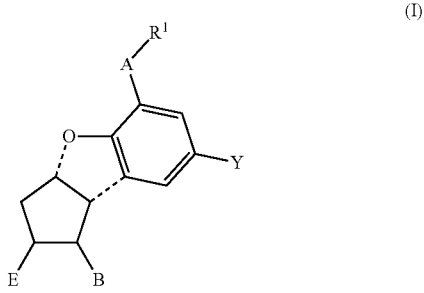

(I)

[wherein $R^1$ is (A) $COOR^2$, wherein $R^2$ is 1) hydrogen or a pharmaceutically acceptable cation, 2) $C_1$-$C_{12}$ straight alkyl or $C_3$-$C_{14}$ branched alkyl, 3) —Z—$R^3$, wherein Z is covalent bond, or straight or branched alkylene represented by $C_tH_{2t}$, wherein t is an integer of 1 to 6, $R^3$ is $C_3$-$C_{12}$ cycloalkyl or $C_3$-$C_{12}$ cycloalkyl substituted with 1 to 3 $R^4$(s) wherein $R^4$ is hydrogen or $C_1$-$C_5$ alkyl, 4) —$(CH_2CH_2O)_nCH_3$, wherein n is an integer of 1 to 5, 5) —Z—$Ar^1$, wherein Z represents the same meanings as described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein the substituent(s) is(are) at least one of chlorine, bromine, fluorine, iodine, trifluoromethyl, $C_1$-$C_4$ alkyl, nitro, cyano, methoxy, phenyl, phenoxy, p-acetamidebenzamide, —CH=N—NH—C(=O)—$NH_2$, —NH—C(=O)-Ph, —NH—C(=O)—$CH_3$ and —NH—C(=O)—$NH_2$), 6) —$C_tH_{2t}COOR^4$, wherein $C_tH_{2t}$ and $R^4$ represent the same meanings as described above, 7) —$C_tH_{2t}N(R^4)_2$, wherein $C_tH_{2t}$ and $R^4$ represent the same meanings as described above, 8) —CH($R^5$)—C—(=O)—$R^6$, wherein $R^5$ is hydrogen or benzoyl, and $R^6$ is phenyl, p-bromophenyl, p-chlorophenyl, p-biphenyl, p-nitrophenyl, p-benzamidephenyl or 2-naphthyl, 9) —$C_pH_{2p}$—W—$R^7$, wherein W is —CH=CH—, —CH=$CR^7$— or —C≡C—, wherein $R^7$ is hydrogen, $C_1$-$C_{30}$ straight or branched alkyl or $C_7$-$C_{30}$ aralkyl, p is an integer of 1 to 5, or 10) —CH($CH_2OR^8$)$_2$, wherein $R^8$ is $C_1$-$C_{30}$ alkyl or acyl, (B) —$CH_2OH$, (C) —C(=O)N($R^9$)$_2$, wherein $R^9$ is hydrogen, $C_1$-$C_{12}$ straight alkyl, $C_3$-$C_{12}$ branched alkyl, $C_3$-$C_{12}$ cycloalkyl, $C_4$-$C_{13}$ cycloalkylalkylene, phenyl, substituted phenyl (wherein the definition(s) of the substituent(s) is(are) the same as those described in (A) 5) mentioned above), $C_7$-$C_{12}$ aralkyl or —$SO_2R^{10}$ wherein $R^{10}$ is $C_1$-$C_{10}$ alkyl, $C_3$-$C_{12}$ cycloalkyl, phenyl, substituted phenyl (wherein the definition(s) of the substituent(s) is(are) the same as those described in (A) 5) mentioned above), or $C_7$-$C_{12}$ aralkyl, wherein the two $R^9$s may be the same or different, with the proviso that when one of them is —$SO_2R^{10}$, the other $R^9$ is not —$SO_2R^{10}$, or (D) —$CH_2OTHP$ (wherein THP is tetrahydropyranyl), A is 1) —$(CH_2)_m$—,

2) —CH=CH—$CH_2$—,

3) —$CH_2$—CH=CH—,

4) —$CH_2$—O—$CH_2$—,

5) —CH=CH—,

6) —O—$CH_2$— or

7) —C≡C—, wherein m is an integer of 1 to 3,

Y is hydrogen, $C_1$-$C_4$ alkyl, chlorine, bromine, fluorine, formyl, methoxy or nitro, B is —X—C($R^{11}$)($R^{12}$)$OR^{13}$, wherein $R^{11}$ is hydrogen or $C_1$-$C_4$ alkyl, $R^{13}$ is hydrogen, $C_1$-$C_{14}$ acyl, $C_6$-$C_{15}$ aroyl, tetrahydropyranyl, tetrahydrofuranyl, 1-ethoxyethyl or t-butyl, X is

1) —$CH_2$—$CH_2$—

2) —CH=CH— or

3) —C≡C—, $R^{12}$ is

1) $C_1$-$C_{12}$ straight alkyl, $C_3$-$C_{14}$ branched alkyl,

2) —Z—$Ar^2$, wherein Z represents the same meanings as described above, $Ar^2$ is phenyl, α-naphthyl, β-naphthyl, or phenyl substituted with at least one substituent selected from the group consisting of chlorine, bromine, fluorine, iodine, trifluoromethyl, $C_1$-$C_4$ alkyl, nitro, cyano, methoxy, phenyl and phenoxy, 3) —$C_tH_{2t}OR^{14}$, wherein $C_tH_{2t}$ represents the same meanings as described above, $R^{14}$ is $C_1$-$C_6$ straight alkyl, $C_3$-$C_6$ branched alkyl, phenyl, phenyl substituted with at least one substituent selected from the group consisting of chlorine, bromine, fluorine, iodine, trifluoromethyl, $C_1$-$C_4$ alkyl, nitro, cyano, methoxy, phenyl and phenoxy, cyclopentyl, cyclohexyl, cyclopentyl substituted with 1 to 4 $C_1$-$C_4$ straight alkyl or cyclohexyl substituted with 1 to 4 $C_1$-$C_4$ straight alkyl, 4) —Z—$R^3$, wherein Z and $R^3$ represent the same meanings as mentioned above, 5) —$C_tH_{2t}$—CH=C($R^{15}$)$R^{16}$, wherein $C_tH_{2t}$ represents the same meanings as mentioned above, $R^{15}$ and $R^{16}$ represent hydrogen, methyl, ethyl, propyl or butyl, or 6) —$C_uH_{2u}$—C≡C—$R^{17}$, wherein u is an integer of 1 to 7, $C_uH_{2u}$ is straight or branched alkylene, and $R^{17}$ is $C_1$-$C_6$ straight alkyl, E is hydrogen or —$OR^{18}$, wherein $R^{18}$ is $C_1$-$C_{12}$ acyl, $C_7$-$C_{15}$ aroyl or $R^2$ (wherein $R^2$ represents the same meanings as described above), the formula includes d-isomers, l-isomers and racemic compounds].

2. The therapeutic agent for uremia in patients suffering from chronic renal failure, according to item 1, wherein in the General Formula (I),
$R^1$ is $COOR^2$, wherein $R^2$ is hydrogen or a pharmaceutically acceptable cation,
A is $-(CH_2)_m-$, wherein m is an integer of 1 to 3,
Y is hydrogen,
B is $-X-C(R^{11})(R^{12})OR^{13}$, wherein $R^{11}$ and $R^{13}$ are hydrogen,
X is $-CH=CH-$,
$R^{12}$ is $-C_uH_{2u}-C\equiv C-R^{17}$ wherein u is an integer of 1 to 7, $C_uH_{2u}$ is straight or branched alkylene, and $R^{17}$ is $C_1$-$C_6$ straight alkyl, and
E is hydrogen or $-OR^2$ (wherein $R^2$ represents the same meanings as described above).

3. The therapeutic agent for uremia in patients suffering from chronic renal failure, according to item 1, wherein in the General Formula (I),
$R^1$ is $COOR^2$, wherein $R^2$ is hydrogen or sodium ion,
A is $-(CH_2)_m-$, wherein m is 3,
Y is hydrogen,
B is $-X-C(R^{11})(R^{12})OR^{13}$, wherein $R^{11}$ and $R^{13}$ are hydrogen,
X is $-CH=CH-$,
$R^{12}$ is $-C_uH_{2u}-C\equiv C-R^{17}$ wherein u is 3, $C_uH_{2u}$ is branched alkylene, and $R^{17}$ is methyl, and
E is $-OH$.

4. A treatment method for ameliorating symptoms of uremia in a patient suffering from chronic renal failure, the method comprising administering the therapeutic agent for uremia according to any one of items 1 to 3 to the patient.

5. Use of the compound represented by General Formula (I) recited in any one of items 1 to 3, for the production of a therapeutic agent for uremia in patients suffering from chronic renal failure.

Effects of the Invention

The therapeutic agent for uremia in patients with chronic renal failure, comprising a compound represented by the General Formula (I), according to the present invention, ameliorates the uremia concurred in patients with chronic renal failure without a side effect, and recovery of reduced appetite, amelioration of activity, increase in weight, and so on are achieved. Further, since the therapy is not by means of physical adsorption of uremic substances and excretion thereof, the present invention provides a therapeutic agent and a treatment method, which agent can be easily taken, and that are not expensive in view of medical economics. The effect of the present invention is clear alleviation or disappearance of symptoms of uremia grasped as clinical symptoms, observed in the state of renal failure, especially even in spite of the state wherein the decrease in renal function is progressed. The prominent effects observed in cats which are a suitable model for evaluation of uremia are comparable to the therapeutic effects obtained by dialysis treatment in human patients with uremia.

BEST MODE FOR CARRYING OUT THE INVENTION

Figure 1:
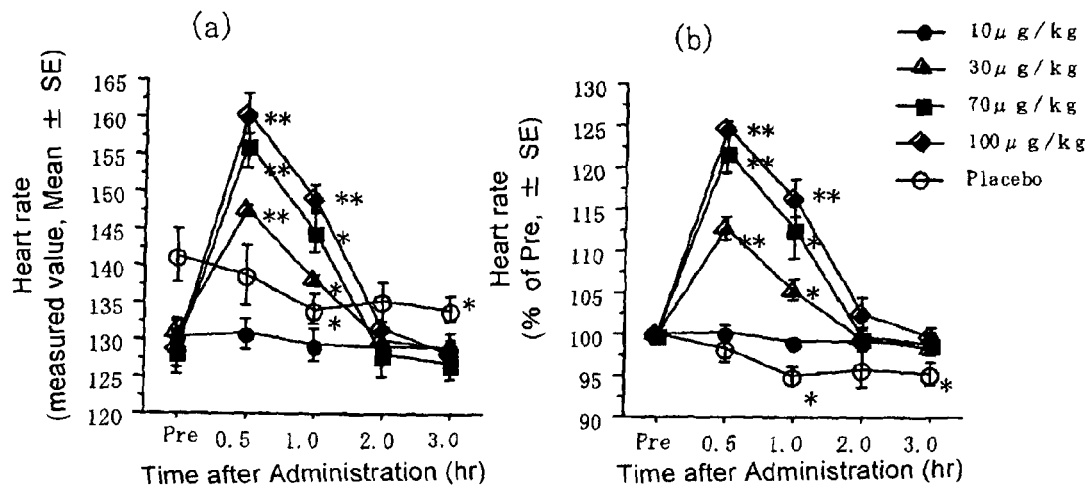
FIG. 1 shows the action of beraprost sodium on the heart rate of healthy cats. Beraprost sodium was orally administered at the dose indicated in the figure. Significant test was carried out by the t-test (paired). *$p<0.05$, ** $p<0.01$. (a) The ordinate in the figure indicates the measured heart rate. The abscissa in the figure indicates the time after administration of beraprost sodium. (b) The ordinate in the figure indicates the relative value taking the heart rate before the administration of beraprost sodium as 100% after adding thereto the % change after administration of beraprost sodium. The abscissa in the figure indicates the time after administration of beraprost sodium.

In the General Formula (I) representing the compounds used as an effective ingredient of the therapeutic agent according to the present invention, $R^1$ is preferably COOH, COONa or COOMe, especially preferably COONa;

A is preferably —$(CH_2)_2$—, —$(CH_3)_3$—, —CH=CH— or —O—$CH_2$—, especially preferably —$(CH_2)_3$—;

Y is especially preferably hydrogen;

B is represented by —X—$C(R^{11})(R^{12})OR^{13}$, wherein $R^{11}$ and $R^{13}$ are especially preferably hydrogen, X is preferably —CH=CH—, especially preferably trans —CH=CH—, $R^{12}$ is preferably hexyl, pentyl, 1-methylpropyl, 2-chlorophenyl, propyloxymethyl, cyclohexyl, 4-hexyn-2-yl, 2-methyl-4-hexyn-2-yl, and especially preferably 4-hexyn-2-yl; and E is especially preferably —OH.

Specific examples of the preferred compounds represented by General Formula (I) include 16-methyl-18,18,19,19-tetrahydro-5,6,7-trinor-4,8-inter-m-phenylene $PGI_2$ (general name: beraprost), 16-methyl-18,18,19,19-tetrahydro-5,6,7-trinor-4,8-inter-m-phenylene $PGI_2$ sodium salt (Sodium rac-(1R,2R,3aS,8bS)-2,3,3a,8b-tetrahydro-2-hydroxy-1-[(E)-(3S,4RS)-3-hydroxy-4-methyloct-1-en-6-ynyl]-1H-cyclopenta[b][1]benzofuran-5-butanoate: general name: beraprost sodium) and the like, and among these, beraprost sodium is preferred. However, these are nothing more than specific examples, and the compounds are not restricted thereto.

In the present invention, the compounds represented by General Formula (I), especially beraprost sodium, are stable for a long time, and bioavailability thereof when orally administered is high. Therefore, they may be especially preferably used because a long-term taking is required for the patients with renal disease, especially patients with chronic renal failure.

The compounds per se represented by the above-described General Formula (I) used in the present invention are known, and can be produced by known methods described in, for example, JP 1-53672 B, JP 7-5582 B, JP 3-7275 A, JP 6-62599 B and so on.

The compounds represented by General Formula (I) according to the present invention may be used individually or two or more of these may be used in combination.

The term "chronic renal failure" in the present invention means that the abnormal state of renal function wherein the number of functional nephron is decreased so that the excretion of nitrogen metabolites is insufficient and homeostasis of internal environment of the body cannot be maintained is continued for a long period of time. Specifically, it may be defined as the state or syndrome wherein blood urea nitrogen (BUN) and/or serum creatinine (Cre) value is(are) continuously elevated. This definition is essentially the same as the definition described in the text books mentioned in the section of Background Art. More specifically, if the serum creatinine value measured by the enzyme method (Tomoko OHARA, Tadashi KAWAI, Kidney and Dialysis, Vol. 39, 1995, 10) is not less than 1.4 mg/dL, the case can be judged as chronic renal failure. However, in cases where the once elevated Cre value is lowered by an existing therapy such as dialysis treatment or the like, the case may be judged as chronic renal failure even if the Cre value is lower than the value mentioned above.

Examples of the primary diseases of the chronic renal failure include renal calculus, urinary obstruction, diabetic nephropathy, acute glomerulonephritis, chronic glomerulonephritis, nephrotic syndrome, polycystic kidney, nephropathy due to infection, lupus nephritis, interstitial nephritis, acute tubulointerstitial nephritis, chronic tubulointerstitial nephritis, liver cirrhosis, hepatic edema and congestive heart failure. The present invention is also effective for uremia whose primary disease is minor glomerular alterating nephritis, focal and segmental glomerulonephritis, diffuse glomerulonephritis, mesangial proliferative glomerulonephritis, diffuse intracanalicular productive nephritis, crescentic nephritis, diffuse sclerotic glomerulonephritis or IgA nephropathy.

The term "uremia" in the present invention means the state or syndrome which shows at least one of nausea, vomiting, anorexia, loss of appetite, weight loss, decreased activity, diarrhea, polydipsia and diuresis, intraoral ulcer, gastrointestinal disorder, urinary retention, cranial neuropathy, circulatory abnormalities, anemia, erythropoietic disorders, skin manifestations and ocular manifestations, caused by the fact that wastes cannot be removed from the blood due to the progress of renal failure. Some text books more simply define uremia as "the condition in which urine exists in the blood", and a separate name "uremic syndromes" is applied to the above-mentioned various symptoms, and the term "uremia" in the present invention includes the various symptoms defined by the uremic syndromes. Examples of the specific syndromes of uremia include encephalopathy and neuropathy due to the urine toxin, in addition to nausea, vomiting, anorexia, weight loss, decreased activity, polydipsia and diuresis, intraoral ulcer, anemia, erythropoietic disorders, loss of appetite and depressed state, and uremia can be grasped by one or more of these syndromes. Thus, the therapeutic agent according to the present invention provides a therapeutic agent for uremia in the patients with chronic renal failure as defined above.

In the evaluation of the effect of the therapeutic agent according to the present invention, the point to which the greatest attention should be paid is not to be sticked to the change of serum Cre value and BUN value. These values are nothing more than markers of renal failure, especially the markers of the filtering function of the kidney for low molecular substances, and they do not reflect the severity of uremia. In fact, according to the present invention, by administering a compound of the General Formula (I), uremic symptoms per se disappear or are ameliorated even under the condition where the renal function is continuously decreased. This response is especially clearly observed in the individuals who have a serum Cre value of not less than 2 mg/dL at the first visit. On the other hand, by the detoxification or the removal of the uremic substances by the compound of the General Formula (I), although the mechanism is unclear, organic regeneration of the kidney occurs and the patient may be freed from renal failure per se. Therefore, monitoring serum Cre value and BUN value during the treatment period is meaningful from this viewpoint.

The patient for whom the therapeutic agent according to the present invention is effective is not restricted, and any subject may be treated as long as the patient is judged to suffer from uremia due to chronic renal failure. The patient is preferably a mammal, more preferably a cat, dog or human. Among these, the therapeutic agent of the present invention shows prominent effects in cats in view of the fact that when beraprost sodium included in the General Formula (I) of the present invention was administered as a therapeutic agent, uremia was ameliorated and side effects such as diarrhea and vomiting were not observed at all during the long dosing period, and that for a cat with light chronic renal failure at a degree of uremia, needless to say the amelioration of the clinical symptoms of uremia, the serum Cre value and BUN value which are renal failure markers drastically decreased and normalized, and the normalized state was continued for a long time, so that restitution effect from the chronic renal failure per se was observed. This discovery is very surprising in view of the fact that chronic renal failure is an irreversible syndrome and the effects of the existing therapeutic drugs are nothing more than delaying the progress of chronic renal failure. In fact, in this particular case according to the present invention, even after a long time from the end of the period of 6 months in which the test compound was administered, the recovered renal function continued to keep the normal values, and the cat was also very healthy when judged from general conditions. The significance of the fact that these findings were obtained not on renal failure model animals, but on actual cases of uremia in patient cats which spontaneously developed chronic renal failure is very great.

The dose per administration of the compound represented by General Formula (I), which is an effective ingredient of the therapeutic agent according to the present invention is usually 0.01 µg/kg to 600 mg/kg, preferably 0.01 µg/kg to 60 mg/kg, still more preferably 0.01 µg/kg to 10 mg/kg, still more preferably 0.03 µg/kg to 3 mg/kg, most preferably 0.1 µg/kg to 1 mg/kg. This dose is preferably administered one to four times a day chronically for not less than 7 days, preferably not less than 30 days, but the way of administration is not restricted thereto.

The pharmaceutical composition according to the present invention can have various dosage forms. More specifically, in case of oral administration, the composition may be in the form of tablets, powders, fine granules, granules, tablets, liquids, syrups, capsules, balls and sprays. Further, shaped products may be coated with a film, coated with sugar or filled in capsules. Preferred examples include tablets, powders, fine granules, granules, tablets, liquids, syrups and capsules. The composition may be in the form of sterilized solution or the like and may be parenterally administered. Other solute(s), such as sodium chloride and glucose in an amount sufficient to make the liquid isotonic may also be used.

In addition to the above-mentioned oral preparations, the therapeutic and prophylactic agent according to the present invention may be used in the form of various injection solutions and suppositories. Depending on the characteristics of the respective drugs, release controls such as those attaining sustained release or delayed release may be applied. For example, sustained releasing function may be given to the drug by a known method, and a pump for sustained-releasing (for example, Alzet minipump) may also be employed, so that a wide variety administration methods may also be employed for parenteral administration. Further, since renal diseases are chronic diseases requiring a long-term therapy, the therapeutic agent according to the present invention may be preliminarily added to the formula meals for the patients with a renal disease under the guidance of a physician or a veterinarian. The therapeutic agent may be orally administered subsequently to, or simultaneously with, or after an interval from the administration of an active carbon preparation which is an existing therapeutic agent for uremia. In cases where the active carbon preparation is administered subsequently to the therapeutic agent according to the present invention, and where the therapeutic agent according to the present invention is administered for a prescribed period prior to the administration of the active carbon preparation, the change from the therapeutic agent of the present invention to the active carbon preparation can be attained almost instantly. On the other hand, in cases where the active carbon preparation is switched to the therapeutic agent of the present invention, an appropriate washout period of the active carbon preparation is preferably given because there is a possibility that the compound represented by General Formula (I) may be adsorbed to the active carbon and its pharmacological effect may be influenced.

The drug of the present invention having the effect to ameliorate uremia may be administered together with the above-described various drugs used for ameliorating renal failure, including angiotensin converting enzyme inhibitors and ATII receptor blockers, as well as antihypertensive drugs such as calcium blockers and β blockers, or a mixture of the therapeutic agent with these drug(s) may be prepared and administered.

The present invention also discloses a treatment method for uremic symptoms in the patients with chronic renal failure. In humans, what can be treated by the method of the present invention are patients with chronic renal failure in whom uremia is complicated. The method may be applied not only to, needless to say, the patients with uremia before receiving dialysis treatment, but also to the patients with uremia who are receiving dialysis treatment. Further, the method may be applied to the patients who developed a complication due to the dialysis treatment, and to the patients who developed side effects by the active carbon preparation. Still further, the method may be employed together with a drug(s) for symptomatic treatment for complications due to dialysis, such as erythropoietin for anemia or erythropoietic disorders. Similarly, the present invention may be applied to the patients with uremia caused by chronic renal failure, who are receiving therapy with active carbon preparation. It should be understood, however, that active carbon has an ability to nonspecifically adsorb substances, and the treatment is preferably performed taking the timing of administration of the both drugs into consideration. In cases where the side effects by the active carbon preparation have been developed, the therapy with active carbon preparation may be stopped and the therapy may be switched to the method of the present invention. Uremia of pet animals other than cats and dogs may also be treated by the present invention in the same way. The pet animals are not restricted, and any of the animals which are the subjects of veterinary medicine, for which diagnosis and therapy are demanded by the clients (owners), and which are judged as uremia caused by chronic renal failure by veterinarians may be treated, and mammals are preferably employed. Animals are classified into families, genera and species in taxonomy, and the present invention may equally applied to any of them. For example, as for cats, although domestic cats (*Felis catus*) are usual, other animals belonging to Family Falidae, genus *Felis* may also be preferably employed. In addition, animals belonging to other genera in Family Felidae, such as genera *Panthera, Acinonyx, Neofelis* and *Lynx* may also be employed. Needless to say, the method of the present invention may also be preferably applied to the animals belonging to the Family Canidae, which are pet animals other than cats and which develop uremia caused by chronic renal failure. Further, needless to say, uremia caused by chronic renal failure of all mammals other than those belonging to the Families Felidae and Canidae can also be treated by the method of the present invention. Needless to say, among the pet animals, the method can be applied not only to the patients with uremia before receiving dialysis treatment, but also to the patients with uremia who have already received dialysis treatment. Further, the method of the present invention may be applied to the patients who have already developed a complication due to dialysis treatment. Still further, the method of the present invention may be applied to the patients who have already developed the side effects by the active carbon preparation. It should be understood, however, that active carbon has an ability to nonspecifically adsorb substances, and the treatment is preferably performed taking the timing and route of administration of the both drugs into consideration.

EXAMPLES

The present invention will now be described more concretely by way of Examples thereof. However, the present invention is not restricted to the following Examples.

Example 1

Preparation of Tablets Containing Beraprost Sodium Influence of Volume and Viscosity of Granulation Solution on Uniformity in Contents in Granules and Tablets As the drug to be administered, beraprost sodium (Sodium rac-(1R,2R, 3aS,8bS)-2,3,3a,8b-tetrahydro-2-hydroxy-1-[(E)-(3S,4RS)-3-hydroxy-4-methyloct-1-en-6-ynyl]-1H-cyclopenta[b][1]benzofuran-5-butanoate) (BPS) was used. Beraprost sodium, 77.5 parts of base powder (lactose (Pharmatose 200M, OMV Japan)) and crystalline cellulose (Avicel PH-101, Asahi Chemicals) 20.0 parts) were fed into a high speed mixing granulation machine, and the mixture was stirred for 1 minutes. Then a preliminarily prepared aqueous solution for granulation containing beraprost sodium and hydroxypropyl cellulose (HPC-M, Shin-Etsu Chemical) as a binder to a final content of 2 parts was added in a prescribed amount, and mixing granulation was carried out. The obtained granules were supplied to a pulverizer and the resultant was dried at 60° C. for 10 hours in hot air. The particle size of the resultant was regulated with a 20-mesh granulator to obtain dry granules. Magnesium stearate was added in an amount of 0.5% based on the dry weight of the granules, and the resultant was mixed in a V-mixer, followed by tableting with a rotary continuous tableting machine using a punch and mortar of 6 mm, 8R to obtain uncoated tablets with a weight of 80 mg/tablet. The obtained uncoated tablets were placed in a coating machine, and coating was performed spraying a coating solution (Opadry™ (Opadry OYS-9607, Japan Colorcon) at 80° C. to obtain tablets coated with a film. The coating amount was 3 mg/tablet, and the contents of beraprost sodium was 40 μg/tablet or 150 μg/tablet.

Example 2

Capsules Containing Beraprost Sodium

The dry granules obtained by the method described in Example 1 were filled into Qualicaps capsules, Size 5, LOK-CAPS, SHIONOGI) to prepare capsules containing granules. Liquid-containing capsules were prepared by diluting beraprost sodium in polyethylene glycol (Wako Pure Chemicals) to attain a dose of 10, 30, 70 or 100 μg/28 μl/kg, and filling the solution into Qualicaps capsules. Beraprost sodium-containing capsules were prepared using a micropipet. Similarly, as a placebo, capsules filled with polyethylene glycol alone in an amount of 28 μl/kg were prepared.

Example 3

Study on Dose of Beraprost Sodium in Healthy Cats

In this study, 3 male cats and 2 female cats, totally 5 Japanese cats, aging 3 to 6 years old were used, which were raised in an animal hospital and for which no abnormalities were observed clinically and by blood test. The subject cats were individually placed in each cage in which each cat was allowed to take water ad libitum, and each cat was fed twice a day after measuring the necessary items. For the purpose of acclimatization, the cats were measured for blood pressure noninvasively twice a day for 2 weeks.

Observations of general clinical symptoms caused by administration of beraprost sodium to healthy cats were performed as follows: Whether adverse events such as ataxia, sedation, lying, suffusion of visible mucosa, lacrimation, hypersalivation, vomiting, diarrhea, incontinence and change in respiratory conditions were expressed or not was observed. Observation was performed before administration, and 30 minutes, 1 hour, 2 hours and 3 hours after each administration during the continuous 7 days in which the drug was administered every day. Each evaluation was performed by rating in 4 ranks as follows: Respiratory conditions were ranked into: no abnormality observed (Grade 0); accelerated respiration (Grade 1); hypopnea (Grade 2); and dyspnea (Grade 3). Ataxia was ranked into: no abnormality observed (Grade 0); slight (Grade 1); moderate (Grade 2); and abasia (Grade 3). Sedation (response to verbal contact) and lying (response to verbal contact) were ranked into: no abnormality observed (Grade 0); slight (Grade 1); moderate (Grade 2); and no response (Grade 3). Evaluations of lacrimation, hypersalivation, vomiting, diarrhea and incontinence were ranked into: no abnormality observed (Grade 0); slight (Grade 1); moderate (Grade 2); and severe (Grade 3).

Blood pressure and heart rate were measured as follows: These were noninvasively measured oscillometrically by using Life Scope 9 produced by NIHON KOHDEN. Systolic pressure, diastolic pressure and heart rate were measured 5 times each before the administration of beraprost sodium and 30 minutes, 1 hour, 2 hours and 3 hours after administration of beraprost sodium at the right foreleg of each cat. From the 5 measured values, the maximum and minimum values were excluded, and the average of the remaining 3 measured values was adopted as the measured value of the individual at the time point. The measurements were carried out every time for 7 days, and the responses by the respective administrations had about the same pattern. In the Example, the results (FIGS. 1 and 2) at the first administration of beraprost sodium are shown as a representative.

Blood test and blood chemical analysis were carried out as follows: Blood was collected before administration of beraprost sodium and on the next day of the termination of continuous administration for 7 days at each dose (the continuous administration of one test compound for 7 days is hereinafter referred to as "1 series") at fasting, and analyzed. Inspection items in the blood test were RBC, WBC, PCV, Hb and Plat, and those in the blood chemical analysis were AST, ALT, T.P, BUN, Cre, Na, K and Cl.

The administration method was as follows: To each of the 5 healthy cats, 4 administration series of beraprost sodium at doses of 10, 30, 70 and 100 μg/kg (continuous administration for 1 week at each dose), respectively, and 1 series of placebo which did not contain beraprost sodium were administered sequentially. In each administration series, the same cat was used in each administration series as the subject cat for the correctness of the evaluation of the test drug. To eliminate the influence of the test drug of the previous series, wash out period of 2 weeks were given after the termination of the respective series. In the beraprost sodium administration series and the placebo administration series, the solution-containing capsules prepared in Example 2 were used. Administration was performed orally at fasting twice a day at intervals of 12 hours for continuous 7 days.

Statistical analysis was carried out using a statistical software Stat View J-4.5 (Abacus Concepts). Since the parameter values before and after the administration to the same individual are compared, significant test was carried out by the paired t-test. In any of the cases, when the significance level was less than 5%, it was judged as significant. The results are as follows:

As a result of observation of clinical symptoms, adverse events were not observed at all in the 10 μg/kg/BID and 30 μg/kg/BID series. On the other hand, 2/5 cases in 70 μg/kg/BID, adverse events such as diarrhea, vomiting and sedation of Grade 1 were sporadically observed during 2 to 6 days after administration. More particularly, Grade 1 diarrhea was observed in cat No. 1 on Day 6 of the continuous administration and in cat No. 2 on Days 2 and 5 of the continuous administration. In the 100 μg/kg/BID series, in all cats, from Day 2 from the start of the administration, Grade 2 vomiting, diarrhea and sedation frequently occurred. More particularly, cat No. 1 showed diarrhea on Days 2 and 3 of continuous administration; cat No. 2 showed diarrhea on Days 2 and 3 and showed diarrhea and vomiting on Day 5; cat No. 3 showed diarrhea and vomiting on Day 2, and diarrhea on Days 3, 4 and 5; cat No. 4 showed diarrhea and vomiting on Day 2, diarrhea on Day 3, vomiting and loose stools on Day 5, and diarrhea on Day 6; and cat No. 5 showed diarrhea and sedation on Day 2, diarrhea and vomiting on Day 3, and diarrhea on Day 4; within 2 hours from the administration of the respective days in each case. As for other adverse clinical symptoms, cat No. 5 in 100 μg/kg/BID series showed sedation on Day 2 of administration. However, these adverse events disappeared by the next day of the final administration.

Except for 10 μg/kg/BID series, significant ($p<0.05$) dose-dependent increase in heart rate due to beraprost sodium was observed from 30 μg/kg/BID, during 30 minutes to 1 hour after the administration of beraprost sodium (FIG. 1(a) shows the actual measured values, FIG. 1(b) shows the rate of change taking the value before administration as 100%). The maximum change was about 25% increase after 30 minutes of the administration of 100 μg/kg. However, with any dose, the heart rate was restored to the level before the administration within 2 hours from the administration. This transient and short-time pattern of increase in the heart rate was the same, either after the first administration or after continuous daily administration of beraprost sodium.

Figure 2:
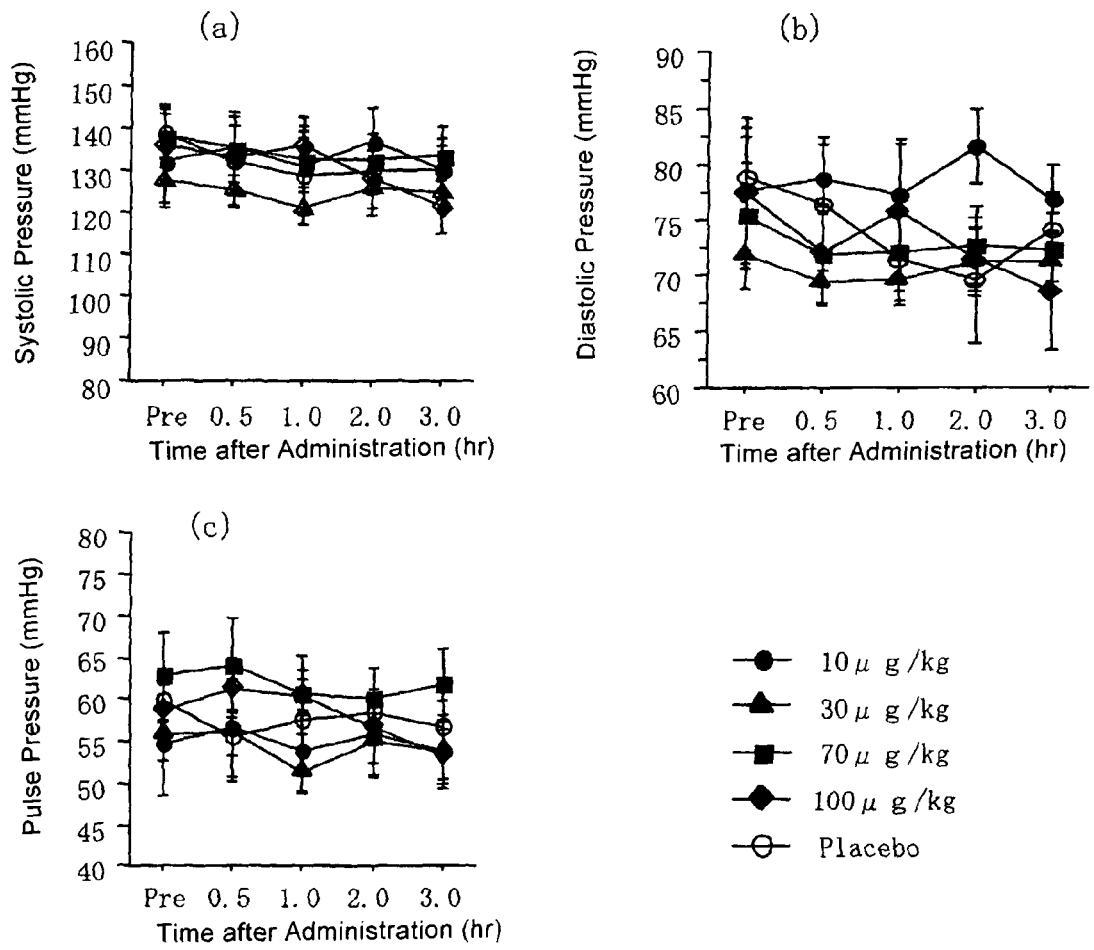
FIG. 2 shows the action of beraprost sodium on the blood pressure (measured value) of healthy cats. Beraprost sodium was orally administered at the dose indicated in the figure. (a) The action of beraprost sodium on systolic pressure is shown. (b) The action of beraprost sodium on diastolic pressure is shown. (c) The action of beraprost sodium on pulse pressure is shown.

The influence on the blood pressure by the first administration in the administration series at respective doses is shown in FIG. 2. No significant change was observed in any of the systolic pressure, diastolic pressure and pulse pressure. As for the blood cell count, electrolytes, renal function and liver function, no adverse change was observed.

Testing methods for the patients showing uremia caused by chronic renal failure, employed in Example 4 or later, will now be described. The criteria and evaluation items for the cats and dogs with chronic renal failure are as follows: Diagnosis of uremia and chronic renal failure were performed totally taking clinical findings (including findings of uremia) and the results of the blood test, blood biochemical analysis and urinalysis into consideration. As the clinical findings of uremia, existence and degree of polydipsia and diuresis, dehydration, anorexia, weight loss, vomiting symptom and state of dehydration were observed. Existence of chronic renal failure was judged based on the serum Cre value as generally employed. As reference data for grasping the degree of progress of chronic renal failure, BUN value was also monitored.

In the blood test, RBC, WBC, PCV, Hg and PLT were measured. In the blood biochemical analysis, TP, Tcho, AST, ALT, ALP, Tbil, BUN, creatinine, calcium, inorganic phosphorus, glucose, sodium ion, potassium ion and chloride ion were measured. In the urinalysis, protein amount, pH, occult blood, bilirubin and glucose were measured. To eliminate the circadian rhythm and influence by meals on the values of blood biochemical markers, every blood collection was carried out in the morning before feeding (at fasting).

As a more specific criterion for chronic renal failure in cats and dogs in the present Examples, a serum Cre value of 1.4 mg/dL in the blood test was employed. Serum Cre value was measured by creatinine deaminase-amidohydrolase method, and the BUN value as reference data for grasping the degree of progress of chronic renal failure was measured by urease-GLDH method.

This pilot clinical test was performed after obtaining informed consent of the owners of the cats (clients) before the start of the test, wherein the clients received explanations about the fact that beraprost sodium had already been approved as a drug for human chronic artery obstruction and had already been marketed, and about the safety thereof. Further, giving first priority to the benefit of the patients and clients, conventional therapeutic methods were also combined appropriately for the individuals with progressed renal failure. Examples of the concomitant drugs employed include synthetic active carbons such as Covalzin, Kremezin and Nefguard; calcium preparations such as calcium carbonate; formula meals such as k/d and low-protein diets; and infusion solutions. However, in cases where there was a rational reason and consent by the owner was obtained, beraprost sodium alone was administered even to the individual with progressed renal failure. On the other hand, drugs thought to influence on the action of beraprost sodium, such as vasodilators (e.g., enalapril), diuretic (e.g., furosemide), drugs which influence on renal blood flow (e.g., dopamine) and steroids (e.g., prednisolone) were not used.

Administration of beraprost sodium was conducted by orally administering the tablet with a content of 150 µg/tablet (Example 1) twice a day (300 µg/head/day). The administration was conducted every day and continued basically for 6 months, and in cases where the owner desired, the administration was continued even after the test period. The Examples of the present invention include both cases where the dosing period was less than 6 months and more than 6 months.

Evaluation of degree of improvement of the uremic symptoms was carried out as follows: From the clinical symptoms related to uremia, activity and appetite, which are unlikely to be overlooked and which can be observed universally from before to after the test period, were selected. The activity was ranked into: disappeared (score 0); decreased (score 1) and normal (score 2), and the appetite was ranked into: lost (score 0); decreased (score 1); slightly decreased (score 2); and normal (score 3). The evaluation was carried out based on the total points (full points were 5 points). Thus, a higher point indicates more improvements in the clinical symptoms.

Example 4

Figure 3:
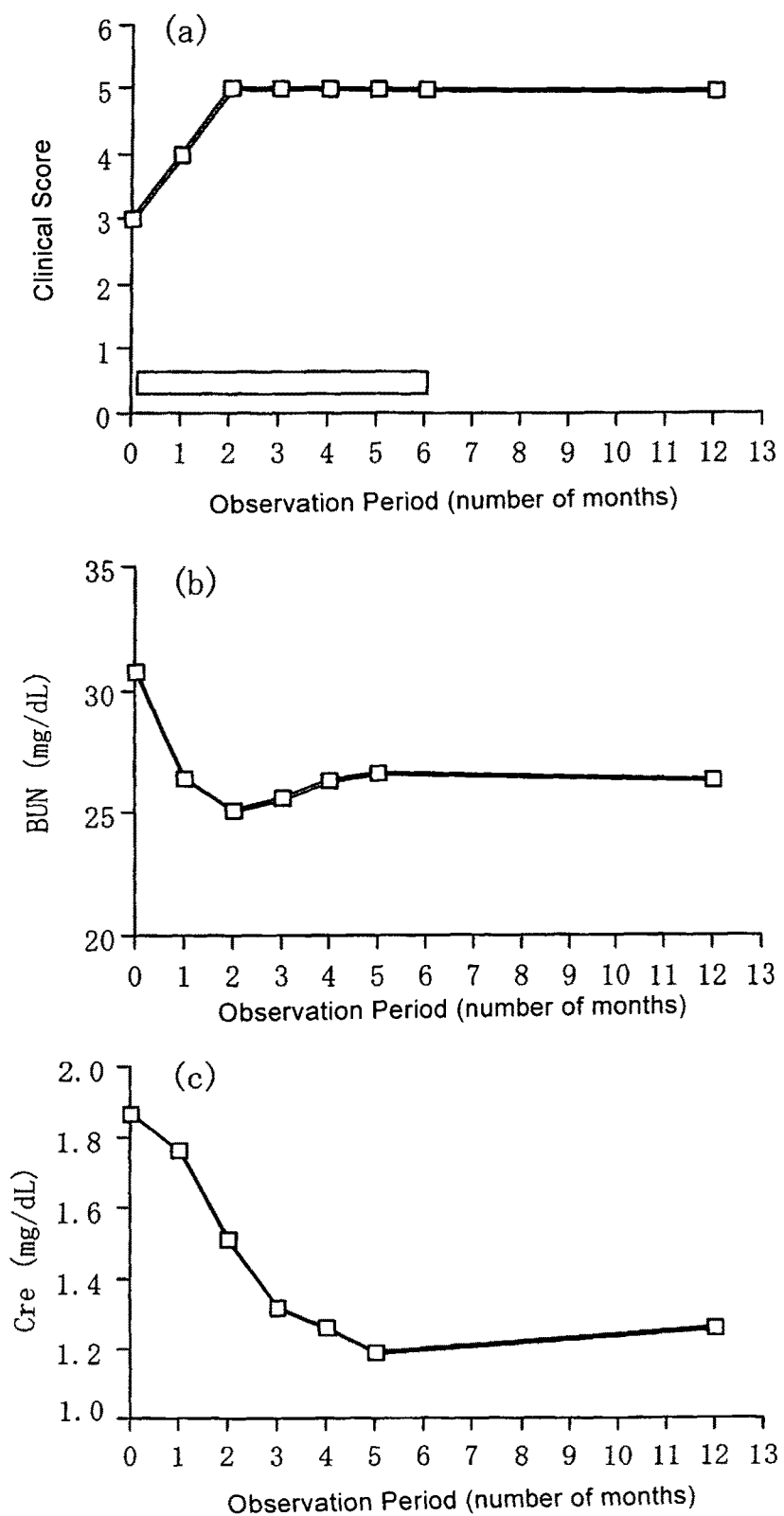
FIG. 3 shows the results of administration of beraprost sodium to a cat with chronic renal failure (Case-A, administration of beraprost sodium alone). In (a), the open bar indicates the dosing period in which beraprost sodium alone was administered. After termination of the administration, no treatment was performed. In the 6th month after termination of the administration of beraprost sodium too, tests were carried out. As a result, uremic symptoms were not observed at all, and the markers of renal function remained within the normal ranges, so that chronic renal failure was cured by the administration of beraprost sodium alone. (a) Effects of amelioration of uremic symptoms (clinical symptoms) by the administration of beraprost sodium alone to the cat (Case-A) with chronic renal failure are shown. The abscissa indicates the number of months after administration of beraprost sodium. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Chronic Renal Failure (Case-A, Administration of Beraprost Sodium Alone, FIG. 3)

Case-A was a male cat of 5 years old, which was diagnosed as chronic renal failure as a result of overall judgment. After obtaining consent of the owner (client), therapy by administration of beraprost sodium alone was started. As a result, the score reached 4 in the first month of the administration of beraprost sodium, and reached 5, the full points, in the second month, and this score was maintained for 6 months which was the dosing period of beraprost sodium. On the other hand, both of BUN and Cre decreased simultaneously with the start of the administration of beraprost sodium, and BUN reached the minimum value in the second month from the start, and serum Cre reached the minimum value in the fifth month from the start. At the end of the 6-month dosing period, there were no differences between the subject and normal cats in terms of clinical observations and biochemical markers. Surprisingly, follow up at 6 months after the termination of the administration of beraprost sodium, that is, at 12 months after the start of the administration, revealed that not only the clinical conditions were very good, but also the BUN and serum Cre value were maintained at normal levels. Thus, in this case, not only the uremia, but also the renal failure itself were completely cured. Although the fact that beraprost sodium restores the once decreased renal function during the administration thereof so that it enables to "relieve" or "restitute" the subject from renal failure is also a novel discovery, the fact that the recovered state is maintained for a long time even after the termination of the administration of beraprost sodium, that is, "the effect that renal failure per se is completely cured and the state is maintained" was totally newly discovered by the present inventors based on this case. During the administration of beraprost sodium, no adverse event such as diarrhea, vomiting or the like was observed at all.

Example 5

Figure 4:
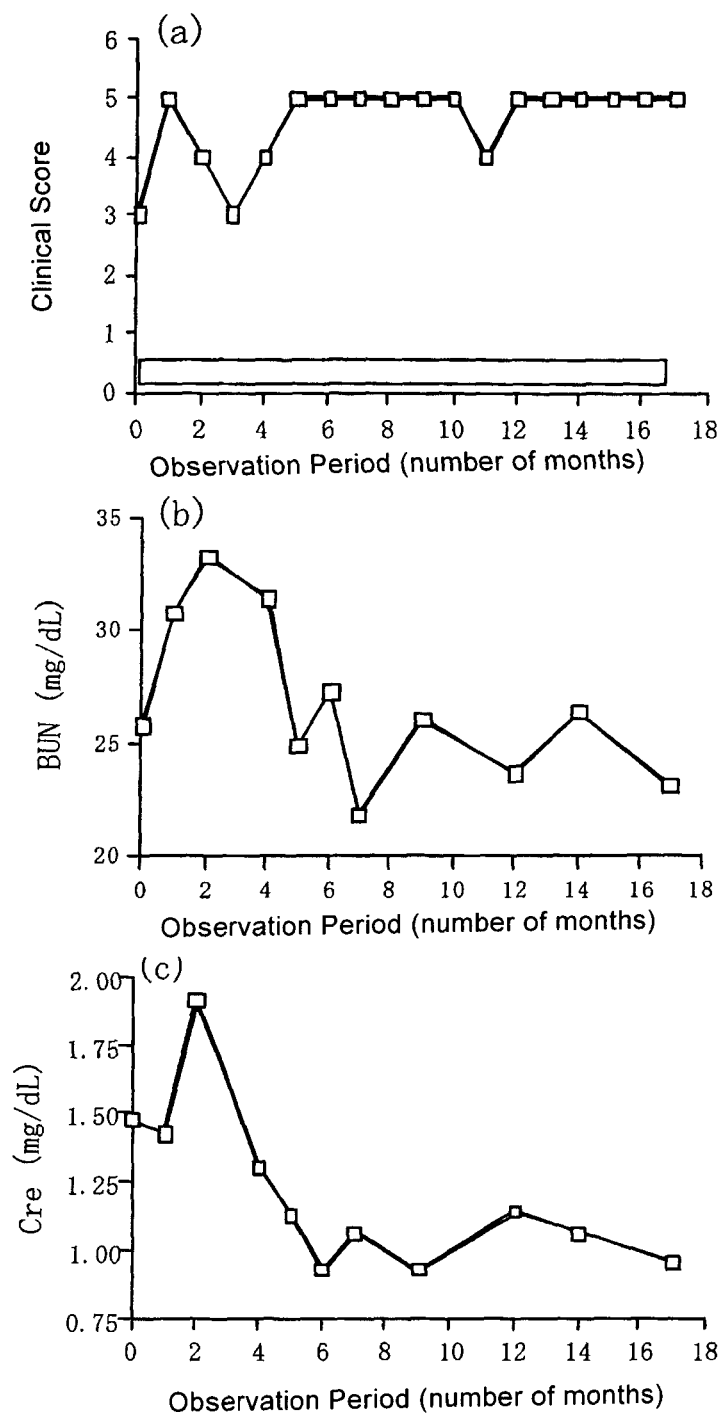
FIG. 4 shows the results of administration of beraprost sodium to a cat with chronic renal failure (Case-B, administration of beraprost sodium alone). (a) Effects of amelioration of uremic symptoms (clinical symptoms) by the administration of beraprost sodium alone to the cat (Case-B) with chronic renal failure are shown. The abscissa indicates the number of months after administration of beraprost sodium. In (a), the open bar indicates the dosing period in which beraprost sodium alone was administered. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Chronic Renal Failure (Case-B, Administration of Beraprost Sodium Alone, FIG. 4)

The subject patient to whom beraprost sodium was to be administered was a male Japanese cat of 4 years old with a body weight of 4.0 kg. The finding at the first visit was urinary retention due to feline lower urinary tract syndromes (FUS). In spite of the treatments with a diuretic and antibiotics, only a temporary lull was obtained and the clinical score was continued to be about 3 points for about 1 year. Thereafter, as a result of overall tests, the cat was diagnosed as chronic renal failure. As a result of the administration of beraprost sodium, the total score of the clinical symptoms at 1 month after the start of administration was increased from 3 points before the administration to 5 points, the full points, so that amelioration was observed. In the present case, during the first to second month from the start of the administration of beraprost sodium, slight amelioration of the clinical symptoms was observed, but there was a tendency that BUN value and serum Cre value increase. However, surprisingly, from the fourth month from the start of the administration of beraprost sodium, BUN value and serum Cre value sharply decreased to the normal values, and the clinical score reached 5 points, the full points. In the present case, apparent correlation between the amelioration of clinical symptoms and the decrease in the values of the markers of renal function was observed. With the amelioration of the uremic symptoms, body weight was increased. In response to the strong demand by the owner (client), the daily administration of beraprost sodium has continued for 1 and half years, but no adverse event has been observed at all, and Cre and BUN are maintained at the normal levels. Thus, it was proved that beraprost sodium can be administered safely for a long time. Further, beraprost sodium not only has an excellent effect to ameliorate uremia, but also it has an effect which is clearly different from the conventional concept of the amelioration of chronic renal failure, which conventional concept is to suppress or stop the progress of the aggravation of renal function. That is, the totally new effect of beraprost sodium which restores the once decreased renal function during the administration thereof so that it enables to "relieve" or "restitute" the subject from renal failure was also discovered in this case too. In this case too, during the administration of beraprost sodium, no adverse event such as diarrhea, vomiting or the like was observed at all.

Example 6

Figure 5:
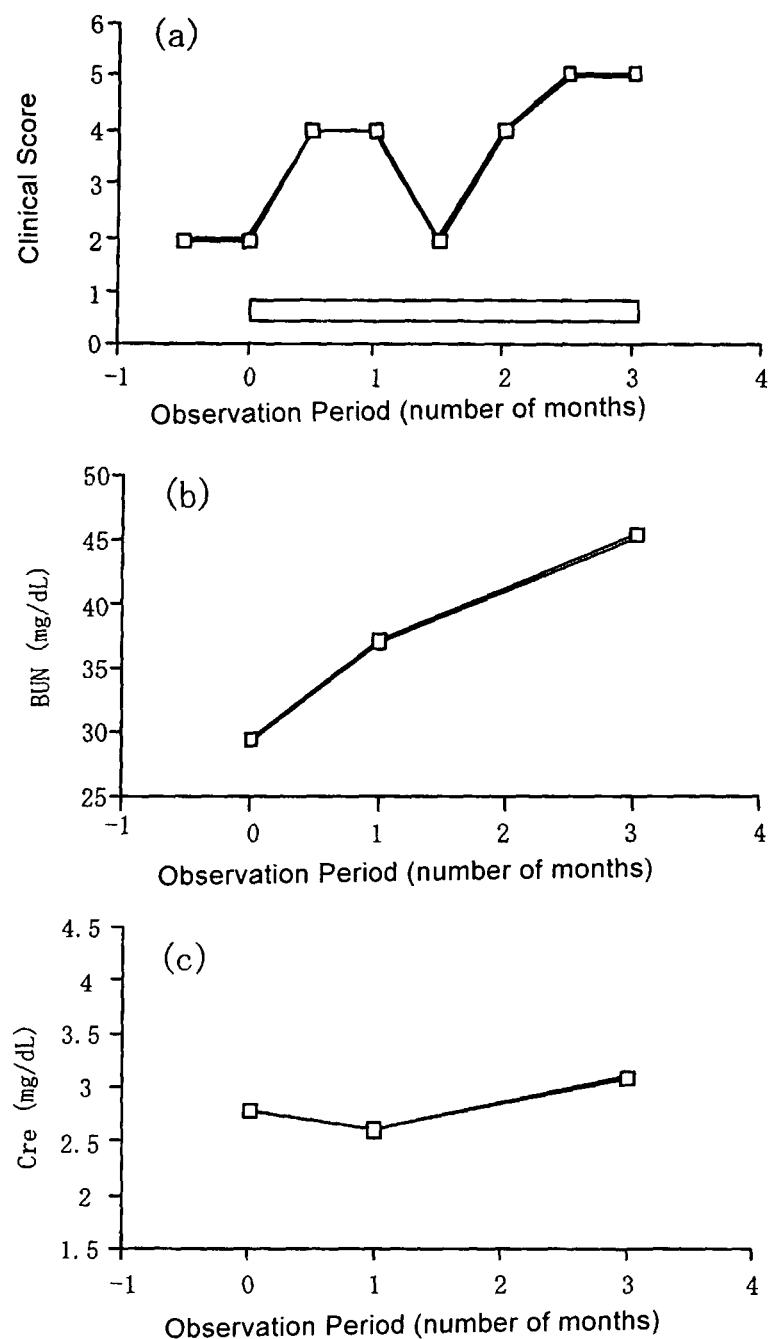
FIG. 5 shows the results of administration of beraprost sodium to a cat with chronic renal failure (Case-C, administration of beraprost sodium alone). (a) Effects of amelioration of uremic symptoms (clinical symptoms) by the administration of beraprost sodium alone to the cat (Case-C) with chronic renal failure are shown. The abscissa indicates the number of months after administration of beraprost sodium. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Chronic Renal Failure (Case-C, Administration of Beraprost Sodium Alone, FIG. 5)

This case was a female cat of 16 years old which was diagnosed as chronic renal failure. Progressed uremia concurred so that it was a case for which other drugs were to be used concomitantly if a conventional therapy was to be applied. However, after extensive explanation to and consent by the owner (client), beraprost sodium alone was administered. At the second week from the start of the administration of beraprost sodium, the clinical score was largely improved from 2 points to 4 points. Although the clinical score was again decreased to 2 points at the sixth week, thereafter, the clinical score was 4 points, and after 2.5 months, the clinical score reached 5 points, the full points. During this period, the serum Cre value did not change or slightly increased, but BUN value continuously increased. By this Example, it was proved that beraprost sodium has an effect to ameliorate uremia even under the condition that the renal failure was not improved in terms of values. In this case too, during the administration of beraprost sodium, no adverse event such as diarrhea, vomiting or the like was observed at all.

Example 7

Figure 6:
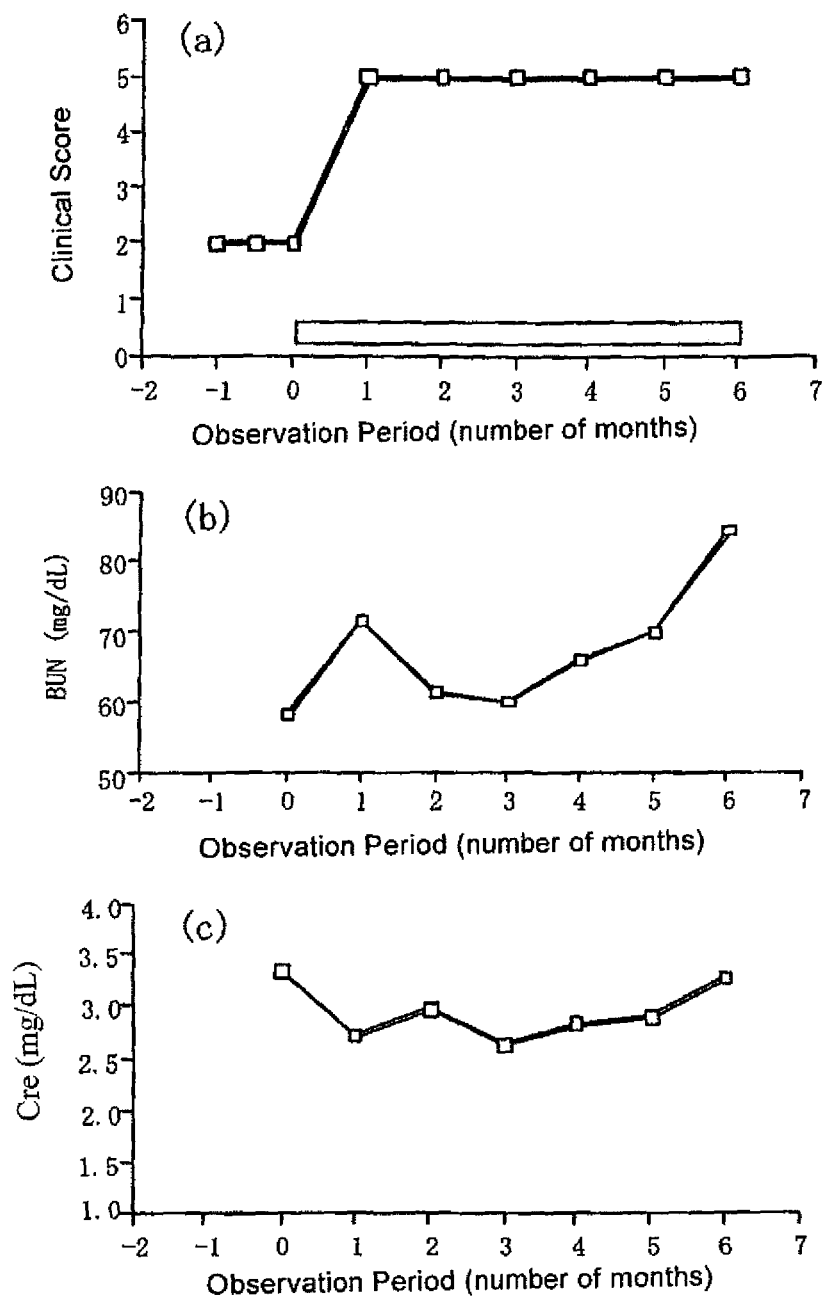
FIG. 6 shows the results of administration of beraprost sodium to a cat with chronic renal failure (Case-D, administration of beraprost sodium alone). In (a), the open bar indicates the dosing period in which beraprost sodium alone was administered. (a) Effects of amelioration of uremic symptoms (clinical symptoms) by the administration of beraprost sodium alone to the cat (Case-D) with chronic renal failure are shown. The abscissa indicates the number of months after administration of beraprost sodium. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Chronic Renal Failure (Case-D, Administration of Beraprost Sodium Alone, FIG. 6)

The subject patient to whom beraprost sodium was to be administered was a male Siamese cat of 17 years old with a body weight of 4.5 kg. Although it was a progressed case, based on the overall judgment, beraprost sodium alone was administered without any conventional therapy such as using a concomitant drug or infusion solution. At one month before the start of administration of beraprost sodium, both appetite and stamina were unstable and the score was 2 points. However, as a result of administration of beraprost sodium, the clinical total score after one month was drastically improved from 2 points before administration to 5 points, and the body weight was also increased. In this case too, during the administration of beraprost sodium, no adverse action causing diarrhea, vomiting or the like was observed at all. On the other hand, BUN value reflecting the renal function was continuously increased even after administration of beraprost sodium. Serum Cre value also kept a high value. In this case too, the effect of beraprost sodium to ameliorate uremia by beraprost sodium per se was clearly observed even though the markers of renal function were not improved. In this case too, during the administration of beraprost sodium, no adverse event such as diarrhea, vomiting or the like was observed at all.

Example 8

Figure 7:
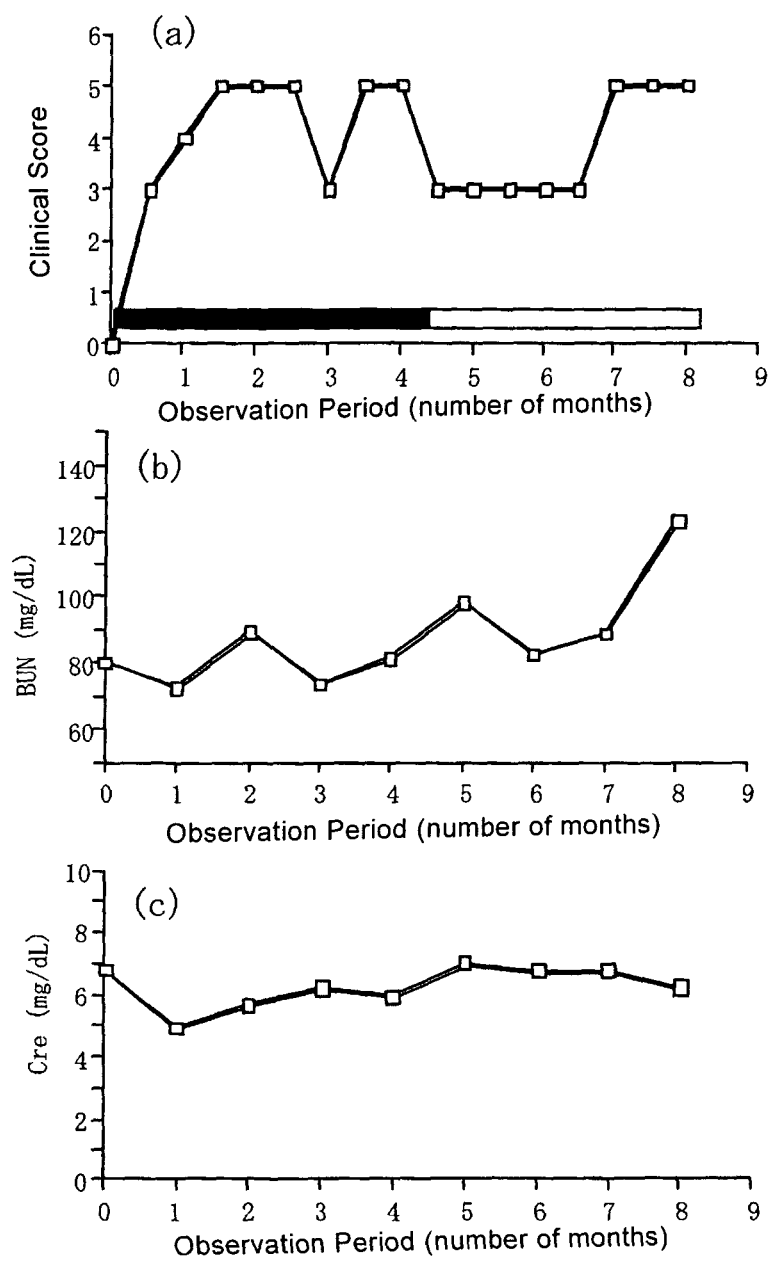
FIG. 7 shows the results of administration of beraprost sodium to a cat with chronic renal failure (Case-E, combination therapy). In (a), the filled bar indicates the period in which treatments with an active carbon preparation, calcium carbonate preparation and k/d meal were combined with the treatment of beraprost sodium. The open bar indicates the period in which administration of the active carbon preparation was not performed because the constipation became severer. (a) Effects of amelioration of uremic symptoms (clinical symptoms) by the administration of beraprost sodium alone to the cat (Case-E) with chronic renal failure are shown. The abscissa indicates the number of months after administration of beraprost sodium. In this case, in addition to the feeding of the formula meal, treatments with the active carbon preparation and calcium carbonate preparation were combined up to an intermediate time point, and thereafter (from 4th month), only the administration of the active carbon preparation was stopped because of severe constipation. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Chronic Renal Failure (Case-E, Combination Therapy, FIG. 7)

The subject patient to whom beraprost sodium was to be administered was a male Japanese cat of 14 years old with a body weight of 3.5 kg. From about 10 years ago, urinary retention and cystitis due to lower urinary tract syndromes (FUS) repeatedly occurred. From several months ago, anorexia and emaciation became prominent, and the cat was diagnosed as renal failure complicated with severe uremia. From several months ago, the cat was treated with 200 mg/BID of Kremezin, diuretic, infusion solution, calcium carbonate preparation and formula meal (k/d meal), but the uremia shown by vomiting, anorexia and loss of activity was not improved at all, and constipation due to the active carbon preparation was also induced. In response to this, Primperan Syrup (Fujisawa Pharmaceutical, general name: metoclopramide) was administered, but the clinical score became 0. In view of this, after obtaining consent by the owner, administration of beraprost sodium was started in addition to the conventional therapies which were treatments with 200 mg/BID of Covalzin, 200 mg/BID of a calcium preparation, formulation meal and infusion solution. The clinical total score after one month from the start of the administration of beraprost sodium was largely increased to 4 points from 0 point before the administration. Thereafter, although there was a temporary decrease in the score, the score was 5 points, the full points, for about 3 months, and the uremic symptoms were largely improved. However, according to the evaluation of renal function during this period, serum Cre value was kept high, and BUN value even continuously increased, so that conditions opposite to the drastic improvement in the uremic symptoms were observed. Since dehydration completely disappeared, infusion became not necessary during this period. Since constipation which is a side effect of Covalzin became severe again 3 months after the start of the treatment, only the administration of Covalzin was eliminated in the fourth months from the combination therapy. From this time point, a low clinical score of 3 points continued for about 2 months, but by the combination therapy including beraprost sodium, the clinical score was restored to 5 points which were the full points from the 7th month to 8th month, so that the uremic symptoms were drastically improved. Surprisingly, at this time point at which the uremic symptoms had been improved, the Cre value was kept high, and BUN value was even largely increased. After stopping the administration of Covalzin, constipation completely disappeared. On the other hand, although administration of beraprost sodium was continued, no adverse events in the digestive tract such as vomiting and diarrhea were not observed at all thereafter. By this, the excellent effect of beraprost sodium to ameliorate uremic symptoms was additionally confirmed clearly in spite of the fact that Cre and BUN which are the renal function markers showing renal failure were still continuously increased. In this case too, during the administration of beraprost sodium, no adverse event such as diarrhea, vomiting or the like was observed at all.

Example 9

Figure 8:
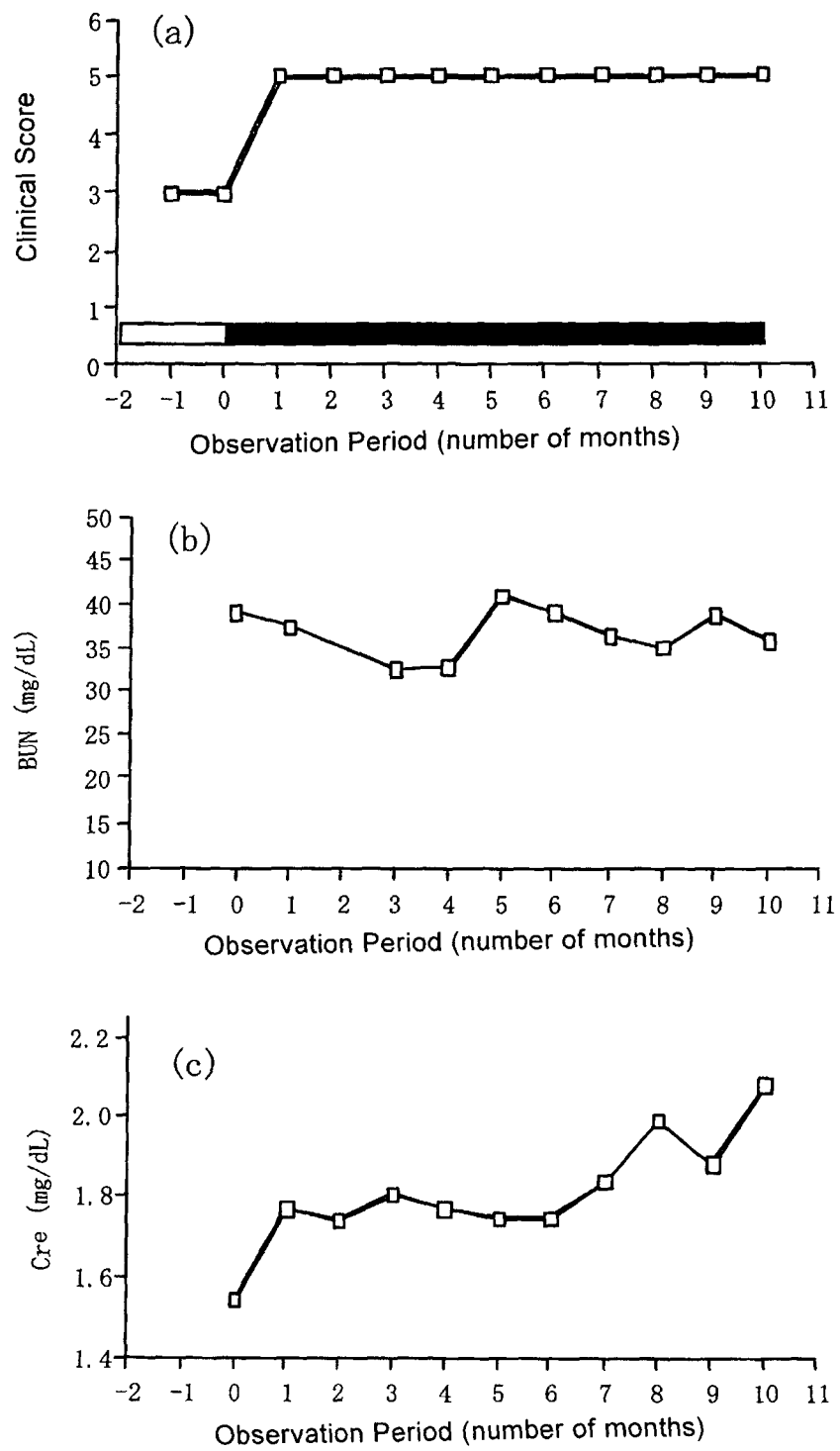
FIG. 8 shows the results of administration of beraprost sodium to a cat with chronic renal failure (Case-F, combination therapy). In (a), the dotted bar indicates the period in which treatments with insulin, an active carbon preparation and a calcium carbonate preparation were combined, and the filled bar indicates the period in which the treatment with beraprost sodium was additionally combined. During the two months before the start of the administration of beraprost sodium, amelioration of uremic symptoms was not observed, but after the start of the administration of beraprost sodium, uremia was quickly improved, and the improved condition was continued. During this period, Cre which is a marker of renal failure continuously increased. (a) Effects of amelioration of uremic symptoms (clinical symptoms) by the administration of beraprost sodium alone to the cat (Case-F) with chronic renal failure are shown. The abscissa indicates the number of months after administration of beraprost sodium. (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Cat with Renal Failure (Case-F, Diabetic Nephropathy, FIG. 8)

The patient was a male cat of 11 years old, was diagnosed as chronic renal failure derived from diabetic nephropathy from the past history and the values obtained by blood biochemical analysis, and showed uremic symptoms. First, for 2 months, insulin (protamine zinc insulin, 2 units/BID) for treating diabetes, and a calcium carbonate preparation and an active carbon preparation for uremia were administered. As a result, as for diabetes, the fasting blood glucose became 100 mg/dL, and the urine sugar was stabilized to ±. However, as for renal failure condition, the BUN value was invariably high, and the uremic symptoms were not improved and the clinical score remained to be 2 to 3 points. In view of this, daily administration of beraprost sodium was started in addition to the insulin therapy and combination therapy with other drugs. As early as in the first month after the start of the administration of beraprost sodium, the clinical symptoms were drastically improved to the score of 5 points which were the full points, and the uremic symptoms disappeared. For 10 months thereafter, this condition continues. On the other hand, BUN value which is a renal failure marker was kept high even after the start of the administration of beraprost sodium, and serum Cre value continuously increased throughout the entire period. By this case, it was proved that beraprost sodium can be safely and effectively used for the therapy of uremia in patients with chronic renal failure whose primary disease is diabetes. Further, it was additionally confirmed actually that beraprost sodium has an effect to ameliorate uremic symptoms even if the renal failure itself is not improved. In this case too, during the administration of beraprost sodium, no adverse event such as diarrhea, vomiting or the like was observed at all.

Example 10

Amelioration of Uremic Symptoms by Tablets with Low Beraprost Sodium Content (Case-G, Administration of Beraprost Sodium Tablets Alone)

The cat with chronic renal failure used in this Example was a cat kept and raised as a transfusion donor for surgeries. By virtue of vaccination at appropriate timings, the cat was free from past history of infectious diseases, and the health condition had been periodically followed by various blood tests. However, by overall judgment, the cat was diagnosed as having transferred to chronic renal failure, and administration of beraprost sodium was started. Since the effectiveness (anti-uremia effect) of administration of beraprost sodium at a dose of 150 μg/head/BID had been confirmed by the information on the previously studied clinical cases, a lower dose of 40 μg/head/BID (Example 1) was administered to this case (case-G), and the tests were carried out every 2 weeks. Before the administration of beraprost sodium, BUN value was 52.2 mg/dL, and the serum Cre value was 2.56 mg/dL. After starting the administration of beraprost sodium at a dose of 40 μg/head/BID, BUN value was almost kept constant, and Cre continuously increased to 2.79 mg/dL on Day 28, and to 3.02 mg/dL on Day 56. On the other hand, increase in body weight was observed from an early stage after the start of the administration of beraprost sodium, and the body weight was increased from 3.2 kg before the administration of beraprost sodium to 3.83 kg on Day 14 and to 3.95 kg on Day 56. Restitution from uremic symptoms was also observed from an early stage, and the score reached 5 points which were the full points as early as on Day 14 from 3 points before the administration of beraprost sodium, and the full points are kept thereafter up to Day 56. Thus, by this Example too, the effect of ameliorating uremic symptoms per se accompanied by chronic renal failure by the administration of beraprost sodium at a lower dose was also confirmed in the condition that the serum Cre value was continuously worsened. In this case too, during the administration of beraprost sodium, no adverse event such as diarrhea, vomiting or the like was observed at all.

Example 11

Increase in Body Weight by Administration of Beraprost Sodium

Administration of beraprost sodium clearly improved appetite and desire for water, and increased body weight. The cases thereof are shown in Table 1. As is apparent from the table, by the administration of beraprost sodium, amelioration and disappearance of uremic symptoms shown by restoration of body weight expressed by an objective value, in addition to the results of the visual observations such as improvement in activity and increase in appetite, gave great satisfaction to the owner not to mention the patient cat.

TABLE 1

Changes in Body Weight of Cats with Renal Failure during Administration of Beraprost Sodium

| | | Changes in Body Weight during Administration of Beraprost Sodium (kg, month) | | | | | | | |
|---|---|---|---|---|---|---|---|---|---|
| Case | Age | −2 | −1 | 0 | 1 | 2 | 3 | 4 | 5 | 6 |
| Case-A | 5 | | | 5.2 | 5.5 | 5.5 | 5.5 | 5.7 | 5.7 | 6.0 |
| Case-B | 4 | | | 3.5 | 3.6 | 3.6 | 3.7 | 3.9 | 4.0 | 4.0 |
| Case-C | 16 | | 2.8 | 2.7 | 2.8 | 2.9 | 2.9 | 2.9 | 3.0 | 3.0 |
| Case-D | 17 | | 4.5 | 4.5 | 4.5 | 4.9 | 4.9 | 4.9 | 4.9 | |
| Case-E | 14 | | | 3.5 | 3.8 | 3.7 | 3.6 | 3.7 | 3.7 | 3.6 |
| Case-F | 11 | | | 4.7 | 5.0 | 5.0 | 5.5 | 5.5 | 5.7 | 5.8 |

Example 12

Figure 9:
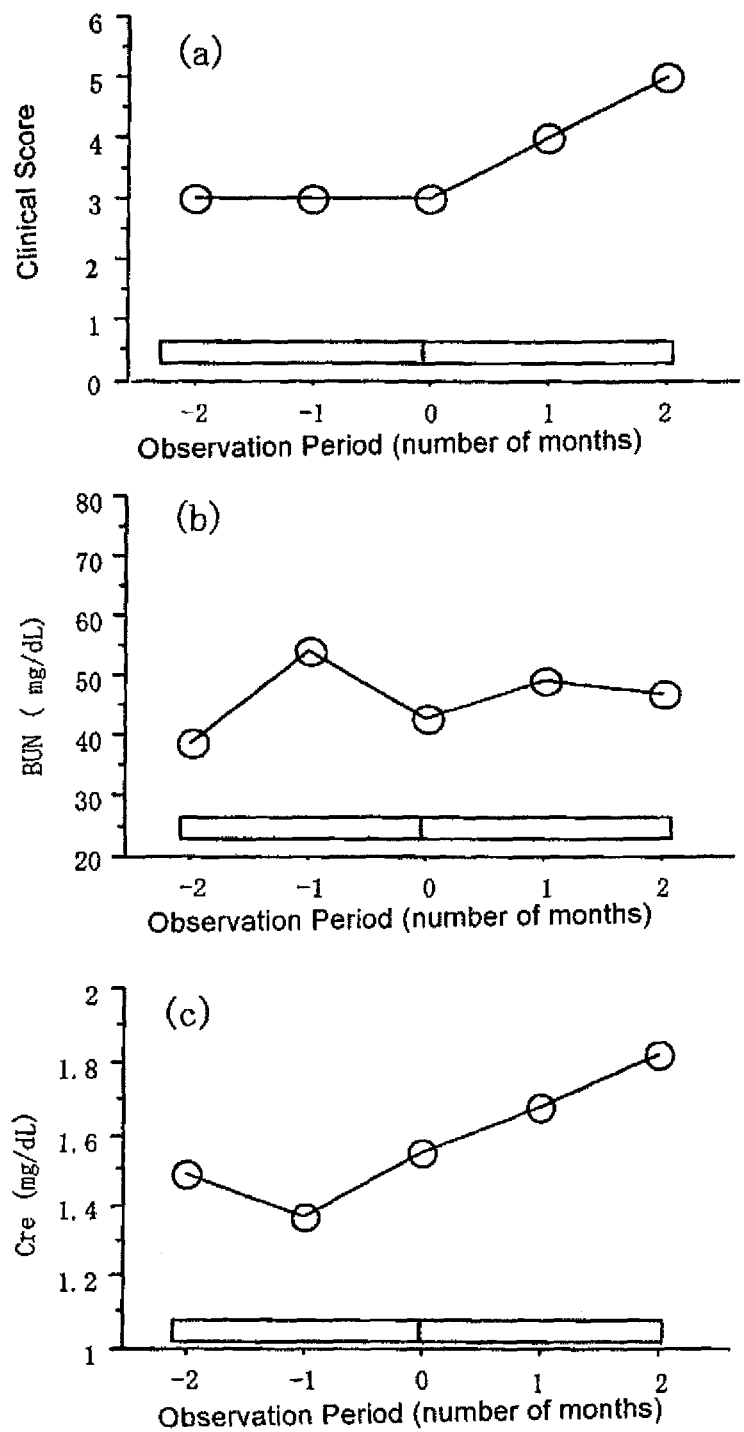
FIG. 9 shows the results of administration of beraprost sodium to a dog with chronic renal failure (Case-H, administration of beraprost sodium alone). In the figure, the dotted bar indicates the treatment period in which an active carbon preparation (Covalzin) alone was administered, and the open bar indicates the treatment period after switching to the administration of beraprost sodium alone. Amelioration of uremic symptoms during the two months in which Covalzin alone was administered was hardly observed, but after the start of administration of beraprost sodium, the uremic symptoms were quickly remitted and ameliorated, and the clinical score reached the full points. However, during this period, Cre which is a marker of renal failure continuously increased. During period of the administration of beraprost sodium, no adverse action causing diarrhea, vomiting or the like was observed at all. (a) Effects of amelioration of uremic symptoms (clinical symptoms) by the administration of beraprost sodium alone to the dog (Case-H) with chronic renal failure are shown. The abscissa indicates the observation period (number of months). (b) The change in BUN value which is a marker of renal function, by the administration of beraprost sodium is shown. (c) The change in serum Cre value which is a marker of renal function, by the administration of beraprost sodium is shown.

Administration of Beraprost Sodium to Dog with Renal Failure (Case-H, FIG. 9)

The subject patient to whom beraprost sodium was to be administered was a female dog (hybrid) of 14 years old with a body weight of 6.4 kg. The patient visited the hospital with chief complaints of anorexia and drastic decrease in activity. Based on the past history, clinical observations and results of clinical test, the dog was diagnosed as chronic renal failure. The clinical score at the first visit was as low as 2 points, and treatment with Covalzin at a dose of 200 mg/BID was started. As a result, although the clinical score was little bit improved to 3 points in 2 weeks, thereafter, the low value of 3 points continued for 2 months, and no more improvement was observed. In view of this, after obtaining consent by the client, treatment with Covalzin was stopped, and switched to administration of beraprost sodium alone. Beraprost sodium was diluted with polyethylene glycol (Wako) to attain a dose of 150 µg/capsule, and was divided into capsules (size 5 Shionogi Qualicaps). Beraprost sodium was orally administered twice a day at fasting. As a result, as shown in FIG. 9, the clinical score was increased to 4 points in the first month from the start of administration, and reached 5 points which were the full points in the second month. On the other hand, BUN which is a renal failure marker did not almost change, and serum Cre value increased in spite of the fact that improvements in the clinical symptoms were drastic after the start of the administration of beraprost sodium. This phenomenon that the improvements in the clinical symptoms and the values of renal failure markers do not necessarily correlate is the same as in cats with renal failure. In the above-described series of therapy, feeding of a formula meal and infusion were not performed at all. In this case too, during the administration of beraprost sodium, no adverse event such as diarrhea, vomiting or the like was observed at all. Based on the above, it was first discovered that in chronic renal failure of dogs, in addition to cats, the effect of beraprost sodium to ameliorate uremic symptoms is clearly shown in spite of the fact that Serum Cre value and BUN value which are markers of renal function indicative of renal failure are continuously worsened.

The invention claimed is:

1. A method of ameliorating symptoms of uremia comprising administering a therapeutic agent comprising beraprost or each isomer constituting beraprost, or a salt thereof as an effective ingredient to an animal belonging to the Family Felidae, wherein an effective dosage is a dosage that does not statistically significantly lower blood pressure.

2. The method according to claim 1, wherein the dose per administration is not more than 100 µg/kg.

3. The method according to claim 1, wherein the dose per administration is 40 to 150 µg/body and wherein the dose per administration is not more than 100 µg/kg.

4. The method according to claim 1, wherein the dose per administration is 12.5 to 55.6 µg/kg.

5. The method according to claim 1, wherein the dose per day is 80 to 300 µg/body and wherein the dose per administration is not more than 100 µg/kg.

6. The method according to claim 1, wherein the dose per day is 25.0 to 111.2 µg/kg.

7. The method according to claim 1, wherein the number of administration is twice daily.

* * * * *